United States Patent
Tateishi et al.

(10) Patent No.: US 7,097,701 B2
(45) Date of Patent: Aug. 29, 2006

(54) PHTHALOCYANINE COMPOUND, INK, INKJET RECORDING METHOD, AND IMAGE FORMING METHOD

(75) Inventors: Keiichi Tateishi, Kanagawa (JP); Yoshiharu Yabuki, Kanagawa (JP); Shigeaki Tanaka, Kanagawa (JP)

(73) Assignee: Fuji Photo Film Co., Ltd., Minami-Ashigara (JP)

( * ) Notice: Subject to any disclaimer, the term of this patent is extended or adjusted under 35 U.S.C. 154(b) by 144 days.

(21) Appl. No.: 10/745,697

(22) Filed: Dec. 29, 2003

(65) Prior Publication Data

US 2005/0132927 A1 Jun. 23, 2005

(30) Foreign Application Priority Data

Dec. 18, 2003 (JP) .................... P.2003-421124

(51) Int. Cl.
*C09D 11/00* (2006.01)
*C07D 487/22* (2006.01)
*B41J 2/01* (2006.01)

(52) U.S. Cl. .................. 106/31.49; 106/31.47; 106/31.46; 106/31.77; 106/31.78; 106/31.76; 540/124; 540/125; 347/100

(58) Field of Classification Search ............. 106/31.49, 106/31.47, 31.46, 31.77, 31.78, 31.76; 540/124, 540/125; 347/100
See application file for complete search history.

(56) References Cited

U.S. PATENT DOCUMENTS

| | | | |
|---|---|---|---|
| 4,657,554 A * | 4/1987 | Reinert et al. ............. | 8/107 |
| 5,322,760 A * | 6/1994 | Itoh et al. ................. | 430/270.1 |
| 6,238,827 B1 * | 5/2001 | Nakazawa et al. ......... | 430/7 |
| 6,384,027 B1 * | 5/2002 | Cook ........................ | 514/189 |
| 2002/0007056 A1 * | 1/2002 | Shimada et al. ........... | 540/124 |
| 2002/0128249 A1 * | 9/2002 | Cook ........................ | 514/185 |
| 2004/0050291 A1 * | 3/2004 | Taguchi et al. ........... | 106/31.27 |
| 2006/0017792 A1 * | 1/2006 | Tateishi et al. ........... | 347/100 |

FOREIGN PATENT DOCUMENTS

| JP | 2003-34758 A | 2/2003 |
|---|---|---|
| WO | WO02/34844 A1 | 5/2002 |

OTHER PUBLICATIONS

English translation of JP 2003/034758; Feb. 2003.*

* cited by examiner

*Primary Examiner*—Helene Klemanski
(74) *Attorney, Agent, or Firm*—Buchanan Ingersoll PC

(57) ABSTRACT

An ink containing a phthalocyanine compound represented by the formula (I):

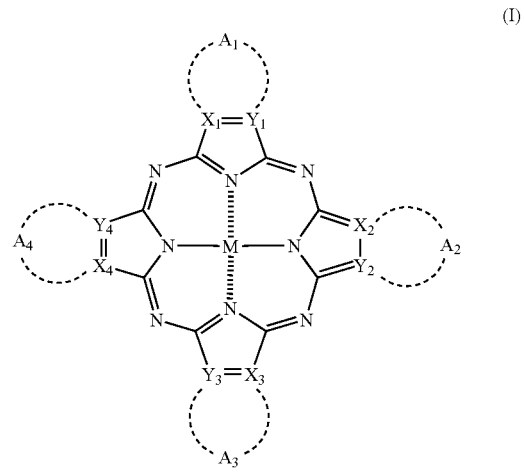

wherein $X_1$ to $X_4$, $Y_1$ to $Y_4$, $A_1$ to $A_4$, and M are defined herein.

9 Claims, No Drawings

PHTHALOCYANINE COMPOUND, INK, INKJET RECORDING METHOD, AND IMAGE FORMING METHOD

FIELD OF THE INVENTION

The invention relates to a novel substituted phthalocyanine compound having improved solubility and excellent hue and fastness and a mixture thereof, an ink containing the phthalocyanine compound (or mixture), an inkjet recording ink (especially a water-soluble ink), a method of improving long-term storage stability of an ink, an inkjet recording method, an image forming method, and a method of improving ozone gas resistance to a colored image material as formed.

BACKGROUND OF THE INVENTION

In recent years, especially materials for forming a color image are the main current as image recording materials. Concretely, recording materials of the inkjet mode, recording materials of the thermal transfer mode, recording materials of the electrophotographic mode, transfer type silver halide photosensitive materials, printing inks, recording pens, and others are extensively utilized. Also, color filters for recording and reproducing a color image are used in imagers such as CCD in photographing instruments and in LCD and PDP in displays.

In these color image recording materials and color filters, for the sake of reproducing or recording a full color image, dyes or pigments of three primary colors of the so-called additive color mixing method or subtractive color mixing method are used. However, it is the present state that fast pigments that have an absorption characteristic such that a preferred color reproduction region can be realized and that are durable against various conditions for use are not available yet, and hence, improvements are eagerly demanded.

The inkjet recording method becomes widespread rapidly and is further developing because the material costs are cheap, high-speed recording is possible, a noise upon recording is small, and color recording is easy.

The inkjet recording method includes the continuous mode of continuously flying droplets and the on-demand mode of flying droplets corresponding to an image information signal; and the ejection mode thereof includes a mode of ejecting droplets upon application of pressure by piezoelectric devices, a mode of ejecting droplets upon generation of bubbles in the ink by heat, a mode of using ultrasonic waves, and a mode of sucking and ejecting droplets by electrostatic force.

Also, as the inkjet recording ink, aqueous inks, oily inks, or solid (melt type) inks are employed.

Pigments that are used for such inkjet recording inks are required such that solubility or dispersibility in solvent is good; high-density recording is possible; hue is good; they are fast to light, heat or active gases in the environment (such as NOx, oxidizing gases such as ozone, and SOx); fastness to water or chemicals is excellent; fixability to image receiving materials is good so that bleeding hardly occurs; preservability as the ink is excellent; they are not toxic; purity is high; and they are cheaply available.

However, it is extremely difficult to seek pigments that meet these requirements at high levels. In particular, it is strongly desired that pigments have good cyan hue and are fast to light, humidity and heat, and especially, pigments are fast to oxidizing gases such as ozone in the environment upon printing on an image receiving material having an ink receiving layer containing porous white inorganic pigment particles. Also, it is strongly desired that the pigments have good ink storage stability as described later.

As a pigment skeleton of cyan to be used for such an inkjet recording ink, those of a phthalocyanine base, an anthraquinone base, and a triphenylmethane base are enumerated, and phthalocyanine compounds having excellent hue and light fastness are used. However, the phthalocyanine compounds do not have sufficient fastness to oxidizing gases, especially ozone and cannot be satisfied with ink stability. Accordingly, improvements are demanded.

As representative phthalocyanine pigments that are most widely reported and utilized, phthalocyanine derivatives classified into the following (1) to (6) groups are enumerated.

(1) Copper phthalocyanine based pigments [for example, $Cu\text{-}Pc\text{-}(SO_3Na)_m$: a mixture of m=1 to 4] such as Direct Blue 86 and Direct Blue 87. Incidentally, the term "Pc" as used in the foregoing formula and the present specification means a phthalocyanine skeleton.

(2) Phthalocyanine based pigments [for example, $Cu\text{-}Pc\text{-}(SO_3Na)_m(SO_2NH_2)_n$: a mixture of (m+N)=1 to 4] such as Direct Blue 199 and those described in JP-A-62-190273, JP-A-63-28690, JP-A-63-306075, JP-A-63-306076, JP-A-2-131983, JP-A-3-122171, JP-A-3-200883, and JP-A-7-138511.

(3) Phthalocyanine based pigments [for example, $Cu\text{-}Pc\text{-}(CO_2H)_m(CONR_1R_2)_n$: (m+n)=a number of from 0 to 4] such as those described in JP-A-63-210175, JP-A-63-37176, JP-A-63-304071, JP-A-5-171085, and WO 00/08102.

(4) Phthalocyanine based pigments [for example, $Cu\text{-}Pc\text{-}(SO_3H)_m(SO_2NR_1R_2)_n$: (m+N)=a number of from 0 to 4, and m≠0] such as those described in JP-A-59-30874, JP-A-1-126381, JP-A-1-190770, JP-A-6-16982, JP-A-7-82499, JP-A-8-34942, JP-A-8-60053, JP-A-8-113745, JP-A-8-310116, JP-A-10-140063, JP-A-10-298463, JP-A-11-29729, JP-A-11-320921, EP173476A2, EP468649A1, EP559309A2, EP596383A1, DE3411476, U.S. Pat. No. 6,086,955, WO 99/13009, and GB2341868A.

(5) Phthalocyanine based pigments [for example, $Cu\text{-}Pc\text{-}(SO_3H)_l(SO_2NH_2)_m(SO_2NR_1R_2)_n$: (l+m+N)=a number of from 0 to 4] such as those described in JP-A-60-208365, JP-A-61-2772, JP-A-6-57653, JP-A-8-60052, JP-A-8-295819, JP-A-10-130517, JP-A-11-72614, JP-T-11-515047, JP-T-11-515048, EP196901A2, WO 95/29208, WP 98/49239, WO 98/49240, WO 99/50363, and WO 99/67334.

(6) Phthalocyanine based pigments [for example, $Cu\text{-}Pc\text{-}(SO_2NR_1R_2)_n$: n=a number of from 1 to 5] such as those described in JP-A-59-22967, JP-A-61-185576, JP-A-1-95093, JP-A-3-195783, EP649881A1, WO 00/08101, and WO 00/08103.

Though the phthalocyanine dyes that are generally used widely at present and described in the above cited patent documents, represented by Direct Blue 87 and Direct Blue 199, are characterized in that they are excellent in light fastness as compared with magenta dyes and yellow dyes, they are liable to generate a problem caused by their solubility. For example, poor solubility is generated at the time of manufacture to cause a manufacture trouble, and a problem caused by deposition of insoluble matters at the time of product storage or use is often generated. In particular, in the inkjet recording as described previously, poor storage stability of inks such as deposition of a dye causes problems inclusive of clogging and poor ejection of printing heads, resulting in marked degradation of a printed image.

Also, these phthalocyanine dyes likely cause color fading by oxidizing gases such as ozone, the matter of which is often taken up as an environmental problem nowadays, leading a serious problem that the printing density greatly lowers.

At present, the inkjet recording is rapidly expanding in its use field. In the future, if it is widely used more and more in general homes, SOHO, business field, etc., it should be exposed to various use conditions or use environment. As a result, there will be often generated problems such that a trouble in the ink storage stability caused by poor solubility of a cyanine dye occurs and that a printed image causes color fading upon exposure to light or active gases in the environment. Accordingly, in particular, realization of pigments and ink compositions having good hue, excellent light fastness or fastness to active gases (such as NOx, oxidizing gases such as ozone, and SOx) in the environment, and high solubility is eagerly demanded more and more.

Up to date, phthalocyanine pigments to which resistance to ozone gas is given have been disclosed in, for example, JP-A-3-103484, JP-A-4-39365, and JP-A-2000-303009. However, it is the present state that any of them cannot satisfy the hue and the fastness to light and oxidizing gases at the same time. In particular, with respect to the resistance to ozone gas, nothing has been reported as to the nature of a pigment as an index thereof. Further, EP1243626A1 and EP1243627A1 report the use of phthalocyanine based pigments. However, it is the present state that since the fastness largely depends upon the density (only high-density areas are made fast), and light is reflected in the high-density areas due to occurrence of a bronze phenomenon, not only the optical density of the recorded image lowers, but also the hue of the recorded image largely differs from the desired hue, so that the required performance cannot be achieved at the satisfactory level.

Also, in the case where an azaphthalocyanine compound described in WO 02/34844 is used as an ink (especially a cyan dye), the hue of the azaphthalocyanine compound is remarkably shifted to short wavelengths. As a result, it cannot satisfy an absorption characteristic upon which a preferred color reproduction region can be realized. Further, when the central metal of a metallic phthalocyanine compound is changed (for example, to Ni), there is an effect of improving the hue (shifting to long wavelengths) to some extent. However, an absorption characteristic upon which a preferred color reproduction region can be realized cannot be satisfied yet, and a further problem occurs with respect to the material safety due to the use of Ni.

On the other hand, as an ink of the inkjet recording mode (the ink will be sometimes referred to as "inkjet recording ink"), aqueous inks are mainly used. The aqueous inks are basically constituted of a pigment, water, and an organic solvent, and from the standpoints of odors and safety to human beings and the circumferential environment, water is the main solvent. Also, as the pigment, water-soluble dyes such as acid dyes, basic dyes, reactive dyes, and direct dyes are generally used.

Such inkjet recording inks (and dyes) are required to have various characteristics described below.
(1) Physical property values of the ink in viscosity, surface tension, specific electric conductivity, density, pH, etc. are proper.
(2) Long-term storage stability of the ink is good.
(3) Dissolution components have high dissolution stability so that clogging of nozzles does not occur.
(4) The ink is quickly dried on a material to be recorded.
(5) The recorded image is clear and good in resistance to light and resistance to water.

However, the conventional inks have not satisfied all of these characteristics yet.

In the case of usually used aqueous inks, water-soluble dyes are used. For that reason, in the case where water splashes on the recorded image, there is generated a big problem in resistance to water such that the dye elutes or the recorded image bleeds or disappears. In particular, occurrence of clogging of heads in the inkjet recording mode is problematic, and at present, various investigations on the ink storage stability as the main purpose are being made.

For example, a method in which an organic solvent or resin is added to an ink using a pigment or an oil-soluble dye as a pigment or an aqueous ink using a water-soluble dye is being investigated. However, the ink using a pigment involves problems such that it is poor in dispersion stability and inferior in storage stability and that it causes clogging of nozzles. Also, since the ink using an oil-soluble dye uses an organic solvent, it involved a problem in environmental hygiene such as odors and a problem such that bleeding of the ink is large, leading to a lowering in image quality. Also, even in the case of inks to which additives have been added, there were involved problems such that the storage stability is inferior, clogging of nozzles occurs, and the inks becomes viscous so that flying of the ink is poor.

The inks disclosed in JP-A-2000-303014 and JP-A-2000-313837 are concerned with phthalocyanine pigments having improved dispersion stability and exhibiting excellent storage stability but cannot meet the hue and the fastness to light and oxidizing gases at the same time. As a result, these inks have not yet become a product that can satisfy the requirements in the market.

Recently, JP-A-6-340835, JP-A-12-239584, and WO 00/08102 describe inks using an aqueous dispersion comprising, as a dispersoid, a polyester resin colored with a dye or a pigment. However, even by utilizing this method, the foregoing problems have not been sufficiently solved yet. On the other hand, it is described that the dye is problematic in affinity with the resin, the matter of which is directly related to a lowering in image density, a lower in resistance to water, storage stability, clogging in nozzles, etc., and control in mean particle size of the colored resin finer particles.

Also, in general, as described in WO 00/17275, WO 00/08103, WO 00/08101, WO 98/41853, and JP-A-10-36471, an unsubstituted phthalocyanine compound is sulfonated, and in the case where it is used as a water-soluble dye, the sulfonated compound is used as an alkali metal salt (such as a sodium slat) thereof as it is. In the case where the sulfonated compound is derived into an oil-soluble dye, those synthesized by subjecting the sulfonated compound to sulfonyl chlorination and then amidation can be used.

In aqueous cyan inks that have hitherto been used for inkjet printing, water-soluble dyes such as copper phthalocyanine compounds comprising a sulfonated copper phthalocyanine compound having a sulfo group or a salt of a sulfo group as a substituent are used.

In that case, not only sulfonation can occur at any position on the phthalocyanine nucleus, but also control of the number of positions to be sulfonated is difficult. Accordingly, in the case of introducing a sulfo group under such reaction conditions, the position and the number of the sulfo group introduced into the product cannot be specified so that a mixture of products that are different in the number and substitution position of a substituent from each other is always obtained.

And the resulting mixture is mingled with a component having low solubility, for example, a component in which the phthalocyanine nucleus is not sulfonated or sulfonated only at one position thereof. As a result, in the case where the product is used as a water-soluble dye, its solubility is insufficient. Thus, improvements in solubility are desired.

On the other hand, phthalocyanine compounds having an ammonium salt of sulfonic acid containing an ion pair of a sulfamoyl group and/or a sulfo group and an amine compound are known as an oil-soluble dye. Such phthalocyanine compounds are produced by chlorosulfonating a metallic phthalocyanine compound with chlorosulfonic acid and reacting the resulting chlorosulfonated compound of the phthalocyanine compound with an amine compound (see, for example, Yutaka Hosoda, *Riron Seizo Senryo Kagaku* (Theoretical Manufacturing Dye Chemistry), 5th Edition, published on Jul. 15, 1968, Gihodo, pp. 798–799). According to this production process, in the reaction of the chlorosulfonated compound of the phthalocyanine compound with the amine compound, not only a sulfonic acid amide group is formed, but also a part of the chlorosulfonyl group is hydrolyzed and remains as a sulfo group, or a phthalocyanine compound containing an ammonium salt of sulfonic acid in wherein a pair ion of the sulfo group and the amine compound is formed is obtained.

In the case where the thus obtained phthalocyanine compound is used as an inkjet recording pigment, there are generated problems such that an ink cannot be prepared because of low solubility of the ink in a solvent and that an ink having a necessary concentration cannot be prepared. Also, due to influences of the residual sulfo group, bleeding occurred when printed on plain paper, resistance to water of the recorded image became worse, or adverse influences in other various characteristics were caused.

In the light of the above, various characteristics of inks, especially inks to be used in the inkjet recording mode largely depend upon characteristics inherent to the pigment, and it is extremely important to select a pigment that meets the foregoing various conditions.

JP-A-2003-34758 discloses a phthalocyanine compound (mixture) containing a pyridine ring, a pyrazine ring and a benzene ring. But, a phthalocyanine compound having more improved fatness (especially, to ozone gas) in which substituents and portions having substituents are limited has been needed.

SUMMARY OF THE INVENTION

A problem of the invention is to solve the foregoing problems of the related-art technologies and to achieve the following objects. That is, the objects of the invention are (1) to provide a novel ink that has an absorption characteristic excellent in color reproducibility and has sufficient fastness to light, heat, humidity and active gases in the environment;

(2) especially, to provide a variety of inks that have the characteristics described above in (1) and can be used as printing inks for inkjet recording, etc.;

(3) further, by the use of the foregoing substituted phthalocyanine compound (or mixture), to provide an inkjet recording ink capable of forming an image having excellent resistance to water, good hue and high fastness to light and active gases in th environment, especially ozone gas and having especially excellent long-term storage stability of ink, an inkjet recording method and a method of improving storage stability of a formed image; and (4) to provide a method of making an image fast by improving resistance to color fading by ozone gas of an image-recorded matter by utilizing the foregoing inkjet recording method.

We, the present inventors made extensive and intensive investigations about phthalocyanine compounds having good hue and solubility and high long-term storage stability as an ink and having high light fastness and gas fastness (especially to ozone gas). As a result, it has been found that the foregoing problems can be solved by a phthalocyanine compound having a specific structure, which has hitherto been unknown (and a mixture thereof), leading to accomplishment of the invention. The means for solving the problems is as follows.

<1> An ink containing a phthalocyanine compound represented by the following formula (I).

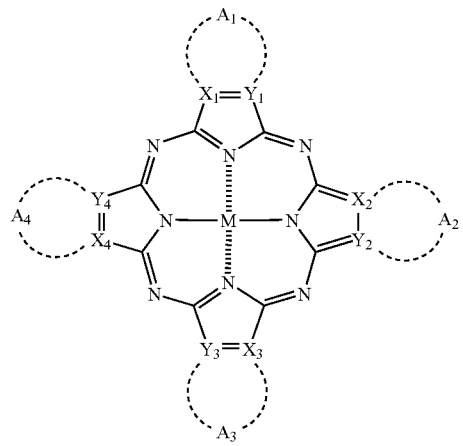

Formula (I)

In the formula (I), $X_1$ to $X_4$ and $Y_1$ to $Y_4$ each independently represents a carbon atom or a nitrogen atom, $A_1$ to $A_4$ each independently represents an atomic group necessary for forming an aromatic ring or a heterocyclic ring, each of which may further form a fused ring together with other ring, together with $X_1$ to $X_4$ and $Y_1$ to $Y_4$, provided that all of four rings constituted of A, X and Y do not represent an aromatic ring at the same time, that in the case where all of four rings constituted of A, X and Y represent a pyridine group at the same time, a pyridine ring in which either one of atoms adjacent to each of X and Y within the pyridine ring represents a nitrogen atom is excluded and that in the case where all of four rings constituted of A, X and Y represent a pyrazine ring at the same time, a pyrazine ring in which both of atoms adjacent to each of X and Y represent a nitrogen atom is excluded; $A_1$ to $A_4$ may each have a substituent; and at least one of $A_1$ to $A_4$, or at least one of substituents of $A_1$ to $A_4$ has an ionically hydrophilic group as a substituent, and M represents a hydrogen atom, a metal element, a metal oxide, a metal hydroxide, or a metal halide.

<2> The ink as set forth above in <1>, wherein the phthalocyanine compound represented by the formula (I) is a phthalocyanine compound represented by the following formula (II).

Formula (II)

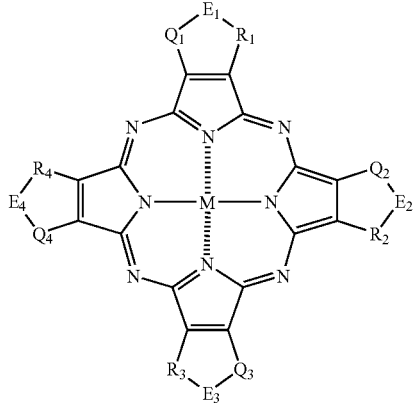

In the formula (II), $Q_1$ to $Q_4$ and $R_1$ to $R_4$ each independently represents a carbon atom, a nitrogen atom, a sulfur atom, an oxygen atom, or a phosphorous atom, $E_1$ to $E_4$ each independently represents an atomic group necessary for forming an aromatic ring or a heterocyclic ring, each of which may further form a fused ring together with other ring, together with $Q_1$ to $Q_4$ and $R_1$ to $R_4$, provided that all of four rings constituted of E, Q and R do not represent an aromatic ring at the same time, that in the case where all of four rings constituted of E, Q and R represent a pyridine group at the same time, a pyridine ring in which either one of Q and R represents a nitrogen atom is excluded and that the case where all of four rings constituted of E, Q and R represent a pyrazine ring at the same time is excluded; $E_1$ to $E_4$ may each have a substituent; and at least one of $E_1$ to $E_4$, or at least one of substituents of $E_1$ to $E_4$ has an ionically hydrophilic group as a substituent, and M is synonymous with that in the formula (I).

<3> The ink as set forth above in <1> or <2>, wherein the phthalocyanine compound represented by the formula (II) is a phthalocyanine compound represented by the following formula (III).

Formula (III)

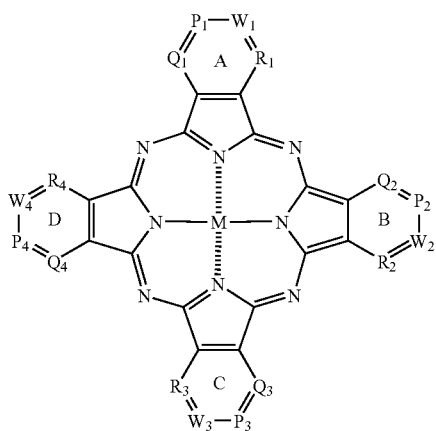

-continued

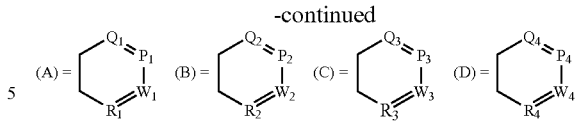

In the formula (III), $Q_1$ to $Q_4$, $P_1$ to $P_4$, $W_1$ to $W_4$, and $R_1$ to $R_4$ each independently represents (=C($J_1$)- and/or —N=), (=C($J_2$)- and/or —N=), (=C($J_3$)- and/or —N=), or (=C($J_4$)- and/or —N=), $J_1$ to $J_4$ each independently represents a hydrogen atom or a substituent, provided that all of four rings {A ring: (A), B ring: (B), C ring: (C), and D ring: (D)} constituted of ($Q_1$, $P_1$, $W_1$, $R_1$), ($Q_2$, $P_2$, $W_2$, $R_2$), ($Q_3$, $P_3$, $W_3$, $R_3$), and ($Q_4$, $P_4$, $W_4$, $R_4$), respectively do not represent an aromatic ring at the same time, that in the case where all of the four rings represent a pyridine ring at the same time, a pyridine ring in which either one of ($Q_1$ and $R_1$), ($Q_2$ and $R_2$), ($Q_3$ and $R_3$), or ($Q_4$ and $R_4$) represents a nitrogen atom is excluded and that in the case where all of the four rings represent a pyrazine group at the same time, a pyrazine ring in which both of ($Q_1$ and $R_1$), ($Q_2$ and $R_2$), ($Q_3$ and $R_3$), or ($Q_4$ and $R_4$) represent a nitrogen atom is excluded; in the case where $J_1$ to $J_4$ each represents a substituent, the substituent may further have a substituent; and at least one of $J_1$ to $J_4$, or at least one of substituents of $J_1$ to $J_4$ has an ionically hydrophilic group as a substituent, and M is synonymous with that in the formula (II).

<4> The ink as set forth above in <3>, wherein in the phthalocyanine compound represented by the formula (III), the heterocyclic ring of at least one the four rings (A), (B), (C) and (D) is represented by the following formula (IV).

Formula (IV)

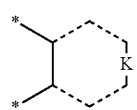

In the formula (IV), K represents an atomic group necessary for forming a 6-membered nitrogen-containing heterocyclic ring.

<5> The ink as set forth above in <3> or <4>, wherein in the phthalocyanine compound represented by the formula (III), at least one (preferably, at least two) of the four rings (A), (B), (C) and (D) represents an aromatic ring, and at least one thereof represents a pyridine ring and/or a pyrazine ring.

<6> The ink set forth above in any one <3> to <5>, wherein in the phthalocyanine compound represented by the formula (III), the aromatic ring of at least one of the four rings (A), (B), (C) and (D) is represented by the following formula (V).

Formula (V)

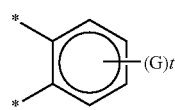

In the formula (V), G represents —SO-$Z_1$, —$SO_2$-$Z_1$, —$SO_2NZ_1Z_2$, —$CONZ_1Z_2$, —$CO_2Z_1$, —$COZ_1$, or a sulfo group.

$Z_1$s' may be the same or different and each represents a substituted or unsubstituted alkyl group having from 1 to 20 carbon atoms in total, a substituted or unsubstituted cycloalkyl group having from 3 to 20 carbon atoms in total, a substituted or unsubstituted alkenyl group having from 2 to 20 carbon atoms in total, a substituted or unsubstituted alkynyl group having from 2 to 12 carbon atoms in total, a substituted or unsubstituted aralkyl group having from 7 to 20 carbon atoms in total, a substituted or unsubstituted aryl group having from 6 to 20 carbon atoms in total, or a substituted or unsubstituted heterocyclic group having from 4 to 20 carbon atoms in total.

$Z_2$s' may be the same or different and each represents a hydrogen atom, a substituted or unsubstituted alkyl group having from 1 to 20 carbon atoms in total, a substituted or unsubstituted cycloalkyl group having from 3 to 20 carbon atoms in total, a substituted or unsubstituted alkenyl group having from 2 to 20 carbon atoms in total, a substituted or unsubstituted alkynyl group having from 2 to 12 carbon atoms in total, a substituted or unsubstituted aralkyl group having from 7 to 20 carbon atoms in total, a substituted or unsubstituted aryl group having from 6 to 20 carbon atoms in total, or a substituted or unsubstituted heterocyclic group having from 4 to 20 carbon atoms in total.

t represents an integer of from 0 to 4 (preferably, t represents an integer of from 1 to 2, and more preferably, t represents an integer of 1), and * represents a binding site to a phthalocyanine skeleton.;

<7> The ink as set forth above in any one of <3> to <6>, wherein an aromatic ring of at least one of the four rings (A), (B), (C) and (D) is represented by the formula (V-1):

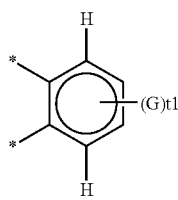

(V-1)

wherein G represents —SO-$Z_1$, —$SO_2$-$Z_1$, —$SO_2NZ_1Z_2$, —$CONZ_1Z_2$, —$CO_2Z_1$, —$COZ_1$, or a sulfo group; t1 represents an integer of from 0 to 2; and * represents a binding site to a phthalocyanine skeleton.

<8> The ink as set forth above in any one of <1> to <7>, wherein the ink is an inkjet recording ink.

<9> An inkjet recording method comprising forming an image on an image receiving material comprising a support having thereon an ink receiving layer containing white inorganic pigment particles using the inkjet recording ink as set forth above in <8>.

<10> An image forming method comprising forming an image using the ink as set forth above in any one of <1> to <7> and the inkjet recording ink as set forth above in <8> and a method of improving resistance to ozone gas of a colored image.

<11> A phthalocyanine compound represented by the following formula (III).

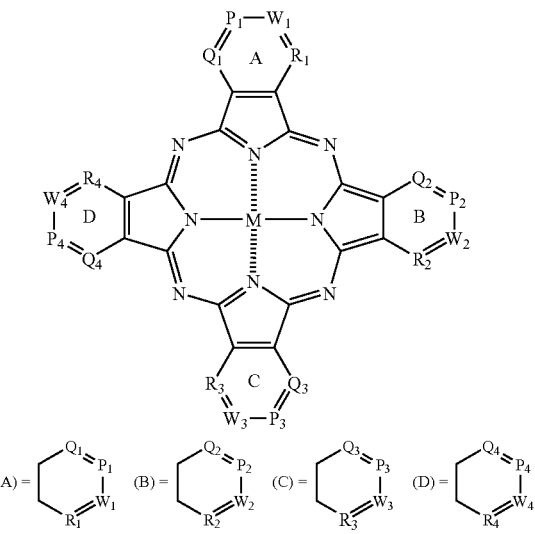

Formula (III)

In the formula (III), $Q_1$ to $Q_4$, $P_1$ to $P_4$, $W_1$ to $W_4$, and $R_1$ to $R_4$ each independently represents (=C($J_1$)- and/or —N=), (=C($J_2$)- and/or —N=), (=C($J_3$)- and/or —N=), or (=C($J_4$)- and/or —N=), $J_1$ to $J_4$ each independently represents a hydrogen atom or a substituent, provided that all of four rings {A ring: (A), B ring: (B), C ring: (C), and D ring: (D)} constituted of ($Q_1$, $P_1$, $W_1$, $R_1$), ($Q_2$, $P_2$, $W_2$, $R_2$), ($Q_3$, $P_3$, $W_3$, $R_3$), and ($Q_4$, $P_4$, $W_4$, $R_4$), respectively do not represent an aromatic ring at the same time, that in the case where all of the four rings represent a pyridine ring at the same time, a pyridine ring in which either one of ($Q_1$ and $R_1$), ($Q_2$ and $R_2$), ($Q_3$ and $R_3$), or ($Q_4$ and $R_4$) represents a nitrogen atom is excluded and that in the case where all of the four rings represent a pyrazine group at the same time, a pyrazine ring in which both of ($Q_1$ and $R_1$), ($Q_2$ and $R_2$), ($Q_3$ and $R_3$), or ($Q_4$ and $R_4$) represent a nitrogen atom is excluded; in the case where $J_1$ to $J_4$ each represents a substituent, the substituent may further have a substituent; and at least one of $J_1$ to $J_4$, or at least one of substituents of $J_1$ to $J_4$ has an ionically hydrophilic group as a substituent, and M is synonymous with that in the formula (II).

DETAILED DESCRIPTION OF THE INVENTION

The invention will be described below in further detail. In the invention, the ink means a composition containing a coloring material such as a dye and a pigment and can be suitably used for image formation.

[Phthalocyanine Compound]

The phthalocyanine compounds represented by the formulae (I), (II) and (III), which are used in the invention, are a substituted phthalocyanine compound (a mixture thereof) in which, for example, at least one specific ring (for example, one represented by the formula (IV)) is introduced into a specific phthalocyanine mother nucleus represented by the formula (III), and at least one specific substituent (for example, one represented by the formula (V)) is introduced into a specific substitution position. In the invention, at the time of synthesis of the phthalocyanine compound, all of possible phthalocyanine mixtures {mixing ratio of the formula (IV) to the formula (V)} may be included, and a specific mixture with a specific mixing ratio {for example, [formula (IV)]/[formula (V)]=from 99.9/0.1 to 0.1/99.1 (eq./eq.)} can be used, or several kinds thereof can be used as a mixture. Therefore, by using a mixture in which plural phthalocyanine compounds having a specific substituent are present, crystallization can be obstructed, and an improvement in storage stability of the pigment (phthalocyanine compound) in the ink can be expected.

In the invention, for the sake of reducing the reactivity with ozone as an electrophilic agent, it is desired to introduce an electron withdrawing group into the phthalocyanine skeleton, thereby making the oxidation potential nobler than 1.0 V (vs SCE). It is preferred that the oxidation potential is noble as far as possible. The oxidation potential is more preferably nobler than 1.05 V (vs SCE), and most preferably nobler than 1.10 V (vs SCE).

The present inventors studied the fastness to ozone gas of a colored image. As a result, it has been noted that there is a correlation between the oxidation potential and the fastness to ozone gas of a compound to be used in the colored image and that when a phthalocyanine compound having an oxidation potential value nobler than 1.0 V against a saturated calomel electrode (SCE) is used, the fastness to ozone gas is further improved.

The reason why the fastness to ozone gas of the colored image is improved can be explained by the relation between HOMO (highest occupied molecular orbital) and LUMO (lowest unoccupied molecular orbital) of the compound and the ozone gas. That is, the coloring compound is oxidized by reaction of HOMO of the colored compound and LUMO of the ozone gas, and as a result, it is considered that the fastness to ozone gas of the colored image lowers. Accordingly, for the sake of improving the fastness to ozone gas, the reactivity with the ozone gas may be lowered by lowering HOMO of the compound.

The oxidation potential value expresses easiness of movement of an electron from a sample to an electrode, and when the value is high (the oxidation potential is noble), the electron hardly moves from the sample to the electrode, in other words, the compound is hardly oxidized. In the relation with the structure of a compound, when an electron withdrawing group is introduced, the oxidation potential becomes nobler, whereas when an electron providing group is introduced, the oxidation potential becomes baser.

While the measurement method of the oxidation potential will be described below in detail, the oxidation potential means a potential at which an electron of a compound is withdrawn at an anode in voltammetry of the compound, and it is considered that the oxidation potential is approximately coincident with the energy level of HOMO in the ground state of the compound.

Those skilled in the art can easy measure the oxidation potential value (Eox). This method is described in, for example, P. Delahay, *New Instrumental Methods in Electrochemistry*, published by Interscience Publishers (1954); A. J. Bard, et al., *Electrochemical Methods*, published by John Willey & Sons (1980); and Akira Fujishima, et al., *Denkikagaku Sokuteiho* (Electrochemical Measurement Method), published by Gihodo (1984).

The measurement of the oxidation potential will be specifically described below. The oxidation potential is obtained by dissolving a test sample in a solvent (such as dimethylformamide and acetonitrile) containing a supporting electrolyte (such as sodium perchlorate and tetrapropylammonium perchlorate) in a concentration of from $1 \times 10^{-4}$ to $1 \times 10^{-6}$ moles/dm$^3$ and measuring a value against SCE (saturated calomel electrode) using cyclic voltammetry or direct current polarography. Also, the supporting electrolyte and solvent to be used can be properly chosen depending upon the oxidation potential and solubility of the test sample. Supporting electrolytes and solvents that can be used are described in Akira Fujishima, et al., *Denkikagaku Sokuteiho* (Electrochemical Measurement Method), published by Gihodo (1984), pages 101 to 118.

The oxidation potential value may possibly be deviated with about several tens mV due to influences of liquid junction potential, liquid resistance of the sample solution, and others. However, by correlating the measured value using a standard sample (for example, hydroquinone), reproducibility of the measure potential value can be guaranteed.

In the invention, as the oxidation potential, a value measured in N,N-dimethylformamide (concentration of compound: $1 \times 10^{-3}$ moles/dm$^3$) containing 0.1 moles/dm$^3$ of tetrapropylammonium perchlorate as a supporting electrolyte using SCE (saturated calomel electrode) as a reference electrode and a graphite electrode as a working electrode by means of direct current polarography is used.

Also, the oxidation potential varies depending upon the structure of a compound. Accordingly, for the sake of lowering the reactivity with ozone as an electrophilic agent, it may be said that it is preferable to choose the structure of a pigment originally having a noble oxidation potential from the viewpoints of not only the fastness to ozone gas but also the matter that an electron withdrawing group or an electron providing group can be arbitrarily introduced for the purpose of adjusting other fastness, hue and physical properties.

For example, for the sake of lowering the reactivity with ozone as an electrophilic agent, with respect to the structure of a compound, it is preferable to make the oxidation potential nobler by (1) introducing a hetero atom (for example, a nitrogen atom) or (2) introducing an electron withdrawing group at an arbitrary position. Accordingly, if a Hammett's substituent constant σp value that is a measure of electron withdrawing properties or electron providing properties of a substituent is used, it is possible to make the oxidation potential nobler by introducing a substituent having a large σp value.

The Hammett's substituent constant σp value will be described below. The Hammett's rule is a rule of thumb advocated by L. P. Hammett in 1935 for the purpose of quantitatively discussing influences of substituents against reaction or equilibrium on benzene derivatives. Now, its appropriateness receive wide recognition. The substituent constant required in the Hammett's rule includes a σp value and a σm value. These values can be found in a number of books. The details are given in, for example, *Lange's Handbook of Chemistry*, 12th Edition, edited by J. A. Dean and published by McGraw-Hill (1979) and *Kagaku No Ryoiki* (Regions of Chemistry), special issue, No. 122, pages 96 to 103, Nankodo (1979).

The present inventors investigated the hue, fastness, crystallinity and storage stability of several kinds of phthalocyanine compounds. As a result, it has been found that by using a phthalocyanine compound (a mixture thereof) in which at least one specific substituent {for example, one represented by the formula (IV)} is introduced into a specific substitution position, and at least one specific substituent {for example, one represented by the formula (V)} is introduced, the foregoing problems can be solved, whereby all of good hue, image fastness and long-term stability with time of an ink liquid can be realized at the same time.

The phthalocyanine compound represented by the following formula (I) that is used in the ink of the invention will be described below in detail.

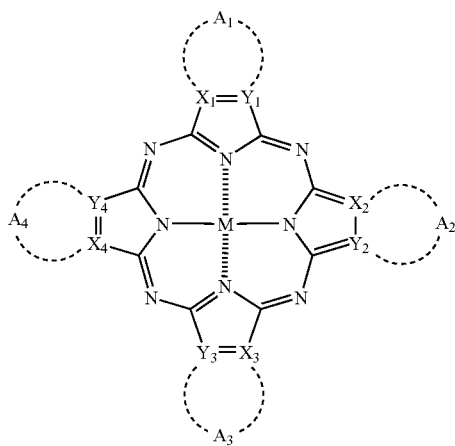

Formula (I)

The phthalocyanine compound represented by the foregoing formula (I) according to the invention includes a compound, its salt and a hydrate thereof.

In the formula (I), $X_1$ to $X_4$ and $Y_1$ to $Y_4$ each independently represents a carbon atom or a nitrogen atom, and preferably a carbon atom. The $X_1$—$Y_1$, $X_2$—$Y_2$, $X_3$—$Y_3$ and $X_4$—$Y_4$ bonds can each take a single bond or a double bond corresponding to the respective atom species and heterocyclic ring species of the following $A_1$ to $A_4$.

In the formula (I), $A_1$ to $A_4$ each independently represents an atomic group necessary for forming an aromatic ring or a heterocyclic ring (each of which may further form a fused ring together with other ring) together with $X_1$ to $X_4$ and $Y_1$ to $Y_4$. The term "aromatic ring" as referred to herein means an aromatic ring composed of only carbon atoms as ring constituting atoms unless otherwise indicated, and specifically, a benzene ring is enumerated. The aromatic ring may be further fused with other aromatic ring, a heterocyclic ring, or an aliphatic ring. In the case where a heterocyclic ring is formed, it is preferable that the atomic group is constituted of at least two kinds selected from a carbon atom, a nitrogen atom, a sulfur atom, and an oxygen atom. Of the heterocyclic groups constituted of $A_1$ to $A_4$, $X_1$ to $X_4$ and $Y_1$ to $Y_4$, a 5- or 6-membered heterocyclic ring is especially preferable. Specific examples of the heterocyclic ring constituted of $A_1$ to $A_4$, $X_1$ to $X_4$ and $Y_1$ to $Y_4$ include pyridine, pyrazine, imidazole, pyrazole, thiazole, isothiazole, oxazole, pyrrole, pyrazolone, indole, isoxazole, thiophene, furan, pyran, penthiophene, quinoline, isoquinoline, pyridazine, pyrimidine, and pyridone. However, all of four rings constituted of A, X and Y do not represent an aromatic ring at the same time. Also, in the case where all of four rings constituted of A, X and Y represent a pyridine group at the same time, a pyridine ring in which either one of atoms adjacent to each of X and Y within the pyridine ring represents a nitrogen atom is excluded. Also, in the case where all of four rings constituted of A, X and Y represent a pyrazine ring at the same time, a pyrazine ring in which both of atoms adjacent to each of X and Y represent a nitrogen atom is excluded.

Also, $A_1$ to $A_4$ may each have a substituent. As the substituent, a halogen atom, an alkyl group, a cycloalkyl group, an alkenyl group, an aralkyl group, an aryl group, a heterocyclic group, a cyano group, a hydroxyl group, a nitro group, an amino group, an alkylamino group, an alkoxy group, an aryloxy group, an amide group, an arylamino group, an ureido group, a sulfamoylamino group, an alkylthio group, an arylthio group, an alkoxycarbonylamino group, a sulfonamide group, a carbamoyl group, a sulfamoyl group, a sulfonyl group, an alkoxycarbonyl group, a heterocyclic oxy group, an azo group, an acyloxy group, a carbamoyloxy group, a silyloxy group, an aryloxycarbonyl group, an aryloxycarbonylamino group, an imido group, a heterocyclic thio group, a sulfinyl group, a phosphoryl group, an acyl group, and an ionically hydrophilic group are preferable. These groups may further have a substituent.

Of these groups, a halogen atom, an alkyl group, a cycloalkyl group, an alkenyl group, an aralkyl group, an aryl group, a heterocyclic group, a cyano group, an alkoxy group, an amide group, an ureido group, a sulfonamide group, a carbamoyl group, a sulfamoyl group, a sulfonyl group, an alkoxycarbonyl group, and an ionically hydrophilic group are more preferable; a halogen atom, an alkyl group, a cycloalkyl group, an alkenyl group, an aralkyl group, an aryl group, a heterocyclic group, a cyano group, a carbamoyl group, a sulfamoyl group, a sulfonyl group, an alkoxycarbonyl group, and an ionically hydrophilic group are especially preferable; and a sulfamoyl group, a sulfonyl group, and an ionically hydrophilic group are most preferable.

At least one of $A_1$ to $A_4$, or at least one of substituents of $A_1$ to $A_4$ has an ionically hydrophilic group as a substituent.

The ionically hydrophilic group as the substituent includes a sulfo group, a carboxyl group, a phosphono group, and a quaternary ammonium group. As the ionically hydrophilic group, a carboxyl group and a sulfo group are preferable, and a sulfo group is especially preferable.

The carboxyl group, the phosphono group, and the sulfo group may be each in the state of a salt. Examples of counter ions capable of forming a salt include an alkali metal ion (such as a lithium ion, a sodium ion, and a potassium ion) and an organic cation (such as a tetramethylguanidium ion).

The alkyl group represented by the substituent that $A_1$ to $A_4$ can have includes an alkyl group having a substituent and an unsubstituted alkyl group. As the alkyl group, an alkyl group having from 1 to 20 carbon atoms when a substituent is eliminated is preferable. Above all, an alkyl group having from 1 to 12 carbon atoms is especially preferable. Especially, from the reason of solubility, a linear alkyl group and/or a branched chain alkyl group each having from 1 to 8 carbon atoms is preferable, and the case where asymmetric carbon is present (used in the form of a racemate) is especially preferable. Examples of the substituent include a hydroxyl group, an alkoxy group, a cyano group, a halogen atom, and an ionically hydrophilic group. Examples of the alkyl group include methyl, ethyl, butyl, isopropyl, t-butyl, hydroxyethyl, methoxyethyl, cyanoethyl, trifluoromethyl, 3-sulfopropyl, and 4-sulfo-butyl.

The cycloalkyl group represented by the substituent that $A_1$ to $A_4$ can have includes a cycloalkyl group having a substituent and an unsubstituted cycloalkyl group. As the cycloalkyl group, a cycloalkyl group having from 3 to 20 carbon atoms when a substituent is eliminated is preferable. Above all, a cycloalkyl group having from 5 to 12 carbon atoms is especially preferable. Especially, from the reason of solubility, a branched chain cycloalkyl group having from 4 to 8 carbon atoms is preferable, and the case where asymmetric carbon is present (used in the form of a racemate) is especially preferable. Examples of the substituent include an ionically hydrophilic group. Examples of the cycloalkyl group include a cyclohexyl group.

The alkenyl group represented by the substituent that $A_1$ to $A_4$ can have includes an alkenyl group having a substituent and an unsubstituted alkenyl group. As the alkenyl group, an alkenyl group having from 2 to 20 carbon atoms when a substituent is eliminated is preferable. Above all, an alkenyl group having from 2 to 12 carbon atoms is especially preferable. Especially, from the reason of solubility, a branched chain alkenyl group having from 3 to 12 carbon atoms is preferable, and the case where asymmetric carbon is present (used in the form of a racemate) is especially preferable. Examples of the substituent include an ionically hydrophilic group. Examples of the alkenyl group include a vinyl group and an allyl group.

The alkynyl group represented by the substituent that $A_1$ to $A_4$ can have includes an alkynyl group having a substituent and an unsubstituted alkynyl group. As the alkynyl group, an alkynyl group having from 2 to 20 carbon atoms when a substituent is eliminated is preferable. Above all, an alkynyl group having from 2 to 12 carbon atoms is especially preferable. Especially, from the reason of solubility, a branched chain alkynyl group having from 4 to 12 carbon atoms is preferable, and the case where asymmetric carbon is present (used in the form of a racemate) is especially preferable. Examples of the substituent include an ionically hydrophilic group.

The aralkyl group represented by the substituent that $A_1$ to $A_4$ can have includes an aralkyl group having a substituent and an unsubstituted aralkyl group. As the aralkyl group, an aralkyl group having from 7 to 20 carbon atoms when a substituent is eliminated is preferable. Above all, an aralkyl group having from 7 to 12 carbon atoms is especially preferable. Especially, from the reason of solubility, a branched chain aralkyl group having from 9 to 12 carbon atoms is preferable, and the case where asymmetric carbon is present (used in the form of a racemate) is especially preferable. Examples of the substituent include an ionically hydrophilic group. Examples of the aralkyl group include a benzyl group and a 2-phenethyl group.

The aryl group represented by the substituent that $A_1$ to $A_4$ can have includes an aryl group having a substituent and an unsubstituted aryl group. As the aryl group, an aryl group having from 6 to 40 carbon atoms is preferable. Above all, an aryl group having from 6 to 12 carbon atoms is especially preferable. Especially, from the reason of solubility, a branched chain aryl group having from 7 to 12 carbon atoms is preferable, and the case where asymmetric carbon is present (used in the form of a racemate) is especially preferable. Examples of the substituent include an alkyl group, an alkoxy group, a halogen atom, an alkylamino group, and an ionically hydrophilic group. Examples of the aryl group include phenyl, p-tolyl, p-methoxyphenyl, o-chlorophenyl, m-(3-sulfo-propylamino)phenyl, and m-sulfophenyl.

The heterocyclic group represented by the substituent that $A_1$ to $A_4$ can have includes a heterocyclic group having a substituent and an unsubstituted heterocyclic group and may further form a fused ring together with other ring. As the heterocyclic ring, a 5- or 6-membered heterocyclic ring is preferable. Also, the heterocyclic group may be an aromatic heterocyclic group or a non-aromatic heterocyclic group.

Examples of the heterocyclic group represented by $A_1$ to $A_4$ (so far as pyridine is concerned, it can be substituted at the 2-position, 3-position or 4-position thereof) include pyridine, pyrazine, pyrimidine, pyridazine, triazine, quinoline, isoquinoline, quinazoline, cinnoline, phthalazine, quinoxaline, pyrrole, indole, furan, benzofuran, thiophene, benzothiophene, pyrazole, imidazole, benzimidazole, triazole, oxazole, benzoxazole, thiazole, benzothiazole, isothiazole, benzisothiazole, thiadiazole, isoxazole, benzisoxazole, pyrrolidine, piperizine, piperazine, imidazoline, and thiazoline.

Above all, an aromatic heterocyclic group is preferable. Preferred examples thereof, when enumerated in the same manner as described previously, include pyridine, pyrazine, pyrimidine, pyridazine, triazine, pyrazole, imidazole, benzimidazole, triazole, thiazole, benzothiazole, isothiazole, benzisothiazole, and thiadiazole.

The halogen atom represented by the substituent that $A_1$ to $A_4$ can have includes a fluorine atom, a chlorine atom, and a bromine atom.

The alkylamino group represented by the substituent that $A_1$ to $A_4$ can have includes an alkylamino group having a substituent and an unsubstituted alkylamino group. As the alkylamino group, an alkylamino group having from 1 to 6 carbon atoms when a substituent is eliminated is preferable. Examples of the substituent include an ionically hydrophilic group. Examples of the alkylamino group include a methylamino group and a diethylamino group.

The alkyloxy group represented by the substituent that $A_1$ to $A_4$ can have includes an alkyloxy group having a substituent and an unsubstituted alkyloxy group. As the alkyloxy group, an alkyloxy group having from 1 to 12 carbon atoms when a substituent is eliminated is preferable. Examples of the substituent include an alkyloxy group, a hydroxyl group, and an ionically hydrophilic group. Examples of the alkyloxy group include a methoxy group, an ethoxy group, an isopropoxy group, a methoxyethoxy group, a hydroxyethoxy group, and a 3-carboxypropoxy group.

The aryloxy group represented by the substituent that $A_1$ to $A_4$ can have includes an aryloxy group having a substituent and an unsubstituted aryloxy group. As the aryloxy group, an aryloxy group having from 6 to 30 carbon atoms is preferable. Examples of the substituent include an alkoxy group and an ionically hydrophilic group. Examples of the aryloxy group include a phenoxy group, a p-methoxyphenoxy group, and an o-methoxyphenoxy group.

The acylamino group represented by the substituent that $A_1$ to $A_4$ can have includes an amide group having a substituent and an unsubstituted amide group. As the acylamino group, an acylamino group having from 2 to 12 carbon atoms when a substituent is eliminated is preferable. Examples of the substituent include an ionically hydrophilic group. Examples of the acylamino group include an acetamide group, a propionamide group, a benzamide group, and a 3,5-disulfobenzamide group.

The arylamino group represented by the substituent that $A_1$ to Acan have includes an arylamino group having a substituent and an unsubstituted arylamino group. As the arylamino group, an arylamino group having from 6 to 30 carbon atoms is preferable. Examples of the substituent include a halogen atom and an ionically hydrophilic group. Examples of the arylamino group include an anilino group and a 2-chloroanilino group.

The ureido group represented by the substituent that $A_1$ to $A_4$ can have includes an ureido group having a substituent and an unsubstituted ureido group. As the ureido group, an ureido group having from 1 to 12 carbon atoms when a substituent is eliminated is preferable. Examples of the substituent include an alkyl group and an aryl group. Examples of the ureido group include a 3-methylureido group, a 3,3-dimethylureido group, and a 3-phenylureido group.

The sulfamoylamino group represented by the substituent that $A_1$ to $A_4$ can have includes a sulfamoylamino group having a substituent and an unsubstituted sulfamoylamino group. Examples of the substituent include an alkyl group. Examples of the sulfamoylamino group include an N,N-dipropylsulfamoylamino group.

The alkylthio group represented by the substituent that $A_1$ to $A_4$ can have includes an alkylthio group having a substituent and an unsubstituted alkylthio group. As the alkylthio group, an alkylthio group having from 1 to 12 carbon atoms when a substituent is eliminated is preferable. Examples of the substituent include an ionically hydrophilic group. Examples of the alkylthio group include a methylthio group and an ethylthio group.

The arylthio group represented by the substituent that $A_1$ to $A_4$ can have includes an arylthio group having a substituent and an unsubstituted arylthio group. As the arylthio group, an arylthio group having from 6 to 30 carbon atoms is preferable. Examples of the substituent include an alkyl group and an ionically hydrophilic group. Examples of the arylthio group include a phenylthio group and a p-tolylthio group.

The alkyloxycarbonylamino group represented by the substituent that $A_1$ to $A_4$ can have includes an alkyloxycarbonylamino group having a substituent and an unsubstituted alkyloxycarbonylamino group. As the alkyloxycarbonylamino group, an alkyloxycarbonylamino group having from 2 to 12 carbon atoms when a substituent is eliminated is preferable. Examples of the substituent include an ionically hydrophilic group. Examples of the alkyloxycarbonylamino group include an ethoxycarbonylamino group.

The sulfonamide group represented by the substituent that $A_1$ to $A_4$ can have includes a sulfonamide group having a substituent and an unsubstituted sulfonamide group. As the sulfonamide group, a sulfonamide group having from 1 to 12 carbon atoms when a substituent is eliminated is preferable. Examples of the substituent include an ionically hydrophilic group. Examples of the sulfonamide group include methanesulfonamide, benzenesulfonamide, and 3-carboxybenzenesulfonamide.

The carbamoyl group represented by the substituent that $A_1$ to $A_4$ can have includes a carbamoyl group having a substituent and an unsubstituted carbamoyl group. Examples of the substituent include an alkyl group. Examples of the carbamoyl group include a methylcarbamoyl group and a dimethylcarbamoyl group.

The sulfamoyl group represented by the substituent that $A_1$ to $A_4$ can have includes a sulfamoyl group having a substituent and an unsubstituted sulfamoyl group. Examples of the substituent include an alkyl group and an aryl group. Examples of the sulfamoyl group include a dimethylsulfamoyl group, a di(2-hydroxyethyl)sulfamoyl group, and a phenylsulfamoyl group.

The sulfonyl group represented by the substituent that $A_1$ to $A_4$ can have includes an alkylsulfonyl group and an arylsulfonyl group. Examples of the sulfonyl group include a 3-sulfopropylsulfonyl group and a 3-carboxypropylsulfonyl group.

The alkoxycarbonyl group represented by the substituent that $A_1$ to $A_4$ can have includes an alkoxycarbonyl group having a substituent and an unsubstituted alkoxycarbonyl group. As the alkoxycarbonyl group, an alkoxycarbonyl group having from 2 to 12 carbon atoms when a substituent is eliminated is preferable. Examples of the substituent include an ionically hydrophilic group. Examples of the alkoxycarbonyl group include a methoxycarbonyl group and an ethoxycarbonyl group.

The heterocyclic oxy group represented by the substituent that $A_1$ to $A_4$ can have includes a heterocyclic oxy group having a substituent and an unsubstituted heterocyclic oxy group. As the heterocyclic oxy group, a heterocyclic oxy group having a 5-membered or 6-membered heterocyclic ring is preferable. Examples of the substituent include a hydroxyl group and an ionically hydrophilic group. Examples of the heterocyclic oxy group include a 2-tetrahydropyranyloxy group.

The azo group represented by the substituent that $A_1$ to $A_4$ can have includes an azo group having a substituent and an unsubstituted azo group. Examples of the azo group include a p-nitrophenylazo group.

The acyloxy group represented by the substituent that $A_1$ to $A_4$ can have includes an acyloxy group having a substituent and an unsubstituted acyloxy group. As the acyloxy group, an acyloxy group having from 1 to 12 carbon atoms when a substituent is eliminated is preferable. Examples of the substituent include an ionically hydrophilic group. Examples of the acyloxy group include an acetoxy group and a benzoyloxy group.

The carbamoyloxy group represented by the substituent that $A_1$ to $A_4$ can have includes a carbamoyloxy group having a substituent and an unsubstituted carbamoyloxy group. Examples of the substituent include an alkyl group. Examples of the carbamoyloxy group include an N-methylcarbamoyloxy group.

The silyloxy group represented by the substituent that $A_1$ to $A_4$ can have includes a silyloxy group having a substituent and an unsubstituted silyloxy group. Examples of the substituent include an alkyl group. Examples of the silyloxy group include a trimethylsilyloxy group.

The aryloxycarbonyl group represented by the substituent that $A_1$ to $A_4$ can have includes an aryloxycarbonyl group having a substituent and an unsubstituted aryloxycarbonyl group. As the aryloxycarbonyl group, an aryloxycarbonyl group having from 7 to 30 carbon atoms is preferable. Examples of the substituent include an ionically hydrophilic group. Examples of the aryloxycarbonyl group include a phenoxycarbonyl group.

The aryloxycarbonylamino group represented by the substituent that $A_1$ to $A_4$ can have includes an aryloxycarbonylamino group having a substituent and an unsubstituted aryloxycarbonylamino group. As the aryloxycarbonylamino group, an aryloxycarbonylamino group having from 7 to 12 carbon atoms when a substituent is eliminated is preferable. Examples of the substituent include an ionically hydrophilic group. Examples of the aryloxycarbonylamino group include a phenoxycarbonylamino group.

The imido group represented by the substituent that $A_1$ to $A_4$ can have includes an imido group having a substituent and an unsubstituted imido group. Examples of the imido group include an N-phthalimido group and an N-succinimido group.

The heterocyclic thio group represented by the substituent that $A_1$ to $A_4$ can have includes a heterocyclic thio group having a substituent and an unsubstituted heterocyclic thio group. As the heterocyclic thio group, a heterocyclic thio group having a 5-membered or 6-membered heterocyclic ring is preferable. Examples of the substituent include an ionically hydrophilic group Examples of the heterocyclic thio group include a 2-pyridylthio group.

The sulfinyl group represented by the substituent that $A_1$ to $A_4$ can have includes an alkylsulfinyl group and an arylsulfinyl group. Examples of the sulfinyl group include a 3-sulfopropylsulfinyl group and a 3-carboxypropylsulfinyl group.

The phosphoryl group represented by the substituent that $A_1$ to $A_4$ can have includes a phosphoryl group having a substituent and an unsubstituted phosphoryl group. Examples of the phosphoryl group include a phenoxyphosphoryl group and a phenylphosphoryl group.

The acyl group represented by the substituent that $A_1$ to $A_4$ can have includes an acyl group having a substituent and an unsubstituted acyl group. As the acyl group, an acyl group having from 1 to 12 carbon atoms when a substituent is eliminated is preferable. Examples of the substituent include an ionically hydrophilic group. Examples of the acyl group include an acetyl group and a benzoyl group.

The ionically hydrophilic group represented by the substituent that $A_1$ to $A_4$ can have includes a sulfo group, a carboxyl group, and a quaternary ammonium group. As the ionically hydrophilic group, a carboxyl group and a sulfo group are preferable, and a sulfo group is especially preferable. The carboxyl group and the sulfo group may be each in the state of a salt. Examples of counter ions capable of forming a salt include an ammonium ion, an alkali metal ion (such as a lithium ion, a sodium ion and a potassium ion) and an organic cation (such as a tetramethylguanidium ion).

It is preferable that the substituted phthalocyanine compound represented by the foregoing formula (I) has an ionically hydrophilic group. The ionically hydrophilic group includes a sulfo group, a carboxyl group, a phosphono group, and a quaternary ammonium group. As the ionically hydrophilic group, a carboxyl group, a phosphono group, and a sulfo group are preferable; and a carboxyl group and a sulfo group are especially preferable. The carboxyl group, the phosphono group, and the sulfo group may be each in the state of a salt. Examples of counter ions capable of forming a salt include an ammonium ion, an alkali metal ion (such as a lithium ion, a sodium ion, and a potassium ion), and an organic cation (such as a tetramethylammonium ion, a tetramethylguanidium ion, and a tetramethylphosphonium ion). Of the counter ions, an alkali metal salt is preferable. A lithium salt is especially preferable because it can enhance the solubility of the compound and improve the ink stability. Those having at least two ionically hydrophilic groups in one molecule of the substituted phthalocyanine compound are preferable, and those having at least two sulfo groups and/or carboxyl groups are especially preferable.

M represents a hydrogen atom, a metal element, a metal oxide, a metal hydroxide, or a metal halide.

Preferred examples of M include a hydrogen atom and a metal element such as Li, Na, K, Mg, Ti, Zr, V, Nb, Ta, Cr, Mo, W, Mn, Fe, Co, Ni, Ru, Rh, Pd, Os, Ir, Pt, Cu, Ag, Au, Zn, Cd, Hg, Al, Ga, In, Si, Ge, Sn, Pb, Sb, and Bi. Above all, Cu, Ni, Zn, and Al are especially preferable, and Cu is most preferable.

Preferred examples of the metal oxide include VO and GeO. Also, preferred examples of the metal hydroxide include $Si(OH)_2$, $Cr(OH)_2$, and $Sn(OH)_2$. Further, preferred examples of the metal halide include AlCl, $SiCl_2$, VCl, $VCl_2$, VOCl, $FeCl_2$, GaCl, and ZrCl.

Also, in the phthalocyanine compound represented by the formula (I), Pc (phthalocyanine ring) may form a dimer (for example, Pc-M-L-M-Pc) or a trimer via L (divalent connecting group). At that time, Ms' that are present may be the same or different.

Preferred examples of the divalent connecting group represented by L include an oxy group —O—, a thio group —S—, a carbonyl group —CO—, a sulfonyl group —$SO_2$—, an imino group —NH—, a methylene group —$CH_2$—, and a group formed by a combination thereof.

Incidentally, with respect to a preferred combination of substituents in the compound represented by the formula (I), compounds in which at least one of the various substituents is the foregoing preferred group are preferable; compounds in which many of the various substituents are the foregoing preferred group are more preferable; and compounds in which all of the substituents are the foregoing preferred group are most preferable.

With respect to the phthalocyanine compound represented by the formula (I), a phthalocyanine compound having a structure represented by the following formula (II) is further preferable. The phthalocyanine compound represented by the formula (II) according to the invention will be described below in detail.

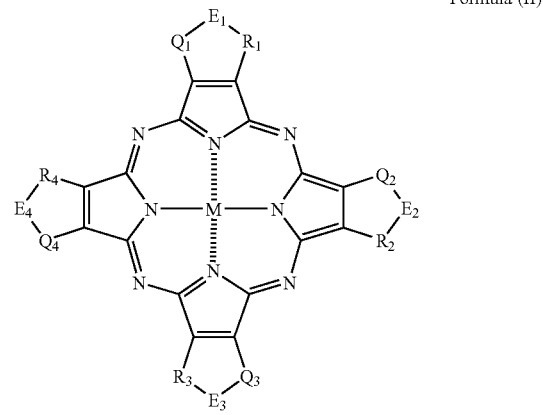

Formula (II)

In the formula (II), $Q_1$ to $Q_4$ and $R_1$ to $R_4$ each independently represents a carbon atom, a nitrogen atom, a sulfur atom, an oxygen atom, or a phosphorous atom, preferably a carbon atom, a sulfur atom, a nitrogen atom, or an oxygen atom, and more preferably a carbon atom, or a nitrogen atom.

$E_1$ to $E_4$ each independently represents an atomic group necessary for forming an aromatic ring or a heterocyclic ring (each of which may further form a fused ring together with other ring) together with $Q_1$ to $Q_4$ and $R_1$ to $R_4$. In the case where a heterocyclic ring is formed, it is preferable that the atomic group is constituted of at least two kinds selected from a carbon atom, a nitrogen atom, a sulfur atom, and an oxygen atom. Also, preferred examples of the heterocyclic ring constituted of $E_1$ to $E_4$, $Q_1$ to $Q_4$ and $R_1$ to $R_4$ are the same as those of the heterocyclic ring constituted of $A_1$ to $A_4$, $X_1$ to $X_4$ and $Y_1$ to $Y_4$ in the foregoing formula (I). However, all of four rings constituted of E, Q and R do not represent an aromatic ring at the same time. Also, in the case where all of four rings constituted of E, Q and R represent a pyridine group at the same time, a pyridine ring in which either one of atoms adjacent to each of Q and R within the pyridine ring represents a nitrogen atom is excluded. Also, the case where all of four rings constituted of E, Q and R represent a pyrazine ring at the same time is excluded.

Also, $E_1$ to $E_4$ may each have a substituent. The substituent is synonymous with the substituent that $A_1$ to $A_4$ in the formula (I) can have, and preferred examples thereof are also the same. These substituents may further have a substituent.

In the case where the phthalocyanine compound represented by the formula (II) is water-soluble, it is preferable that the phthalocyanine compound has an ionically hydrophilic group. The ionically hydrophilic group includes a sulfo group, a carboxyl group, a phosphono group, and a quaternary ammonium group. As the ionically hydrophilic group, a carboxyl group, a phosphono group, and a sulfo group are preferable; and a carboxyl group and a sulfo group are preferable. The carboxyl group, the phosphono group, and the sulfo group may be each in the state of a salt. Examples of counter ions capable of forming a salt include an ammonium ion, an alkali metal ion (such as a lithium ion, a sodium ion, and a potassium ion), and an organic cation (such as a tetramethylammonium ion, a tetramethylguanidium ion, and a tetramethylphosphonium ion). Of the counter ions, an alkali metal salt is preferable. A lithium salt is especially preferable because it can enhance the solubility of the compound and improve the ink stability. Those having at least two ionically hydrophilic groups in one molecule of the substituted phthalocyanine compound are preferable, and those having at least two sulfo groups and/or carboxyl groups are especially preferable.

With respect to the phthalocyanine compound represented by the formula (II), an especially preferred combination of substituents is the same as the especially preferred combination of substituents in the formula (I).

Incidentally, with respect to a preferred combination of substituents in the compound represented by the formula (II), compounds in which at least one of the various substituents is the foregoing preferred group are preferable; compounds in which many of the various substituents are the foregoing preferred group are more preferable; and compounds in which all of the substituents are the foregoing preferred group are most preferable.

With respect to the phthalocyanine compound represented by the formula (II), a phthalocyanine compound having a structure represented by the following formula (II) is further preferable. The phthalocyanine compound represented by the formula (III) according to the invention will be described below in detail.

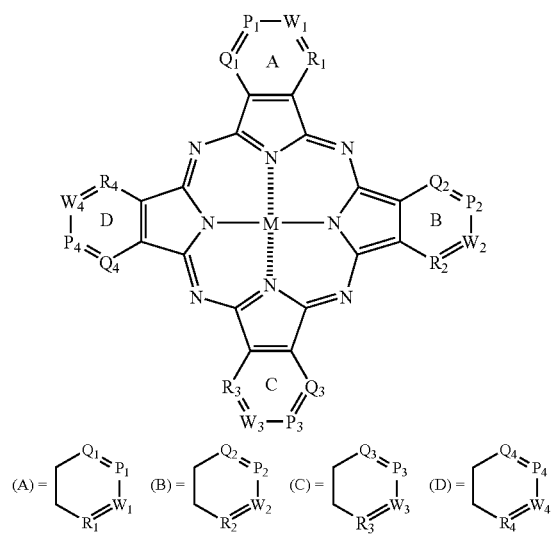

Formula (III)

In the formula (III), $Q_1$ to $Q_4$, $P_1$ to $P_4$, $W_1$ to $W_4$, and $R_1$ to $R_4$ each independently represents (=C($J_1$)- and/or —N=), (=C($J_2$)- and/or —N=), (=C($J_3$)- and/or —N=), or (=C($J_4$)- and/or —N=), However, all of four rings {A ring: (A), B ring: (B), C ring: (C), and D ring: (D)} constituted of ($Q_1$, $P_1$, $W_1$, $R_1$), ($Q_2$, $P_2$, $W_2$, $R_2$), ($Q_3$, $P_3$, $W_3$, $R_3$), and ($Q_4$, $P_4$, $W_4$, $R_4$), respectively do not represent an aromatic ring at the same time.

M is synonymous with that in the formula (II), and preferred examples thereof are also the same.

Especially, a phthalocyanine compound in which at least one of rings {A ring; (A), B ring: (B), C ring: (C), and D ring: (D)} constituted of ($Q_1$, $P_1$, $W_1$, $R_1$), ($Q_2$, $P_2$, $W_2$, $R_2$), ($Q_3$, $P_3$, $W_3$, $R_3$), and ($Q_4$, $P_4$, $W_4$, $R_4$) represents a nitrogen-containing heterocyclic ring is preferable.

$J_1$ to $J_4$ each independently represents a hydrogen atom or a substituent.

Also, in the case where $J_1$ to $J_4$ each represents a substituent, the substituent may further have a substituent. However, at least one of $J_1$ to $J_4$, or at least one of substituents of $J_1$ to $J_4$ has an ionically hydrophilic group as a substituent.

Further, a phthalocyanine compound in which at least one of rings {A ring: (A), B ring: (B), C ring: (C), and D ring: (D)} constituted of ($Q_1$, $P_1$, $W_1$, $R_1$), ($Q_2$, $P_2$, $W_2$, $R_2$), ($Q_3$, $P_3$, $W_3$, $R_3$), and ($Q_4$, $P_4$, $W_4$, $R_4$) represents a nitrogen-containing heterocyclic ring represented by the following formula (IV) is preferable.

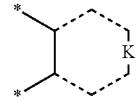

Formula (IV)

However, in the case where all of four rings {A ring: (A), B ring: (B), C ring: (C), and D ring: (D)} represent a pyridine ring at the same time, a pyridine ring in which either one of ($Q_1$ and $R_1$), ($Q_2$ and $R_2$), ($Q_3$ and $R_3$), or ($Q_4$ and $R_4$) represents a nitrogen atom is excluded.

Also, the case where all of four rings {A ring: (A), B ring: (B), C ring: (C), and D ring: (D)} represent a pyrazine ring at the same time is excluded Further, it is preferable that at least one (preferably, at least two) of rings {A ring: (A), B ring: (B), C ring: (C), and D ring: (D)} constituted of ($Q_1$, $P_1$, $W_1$, $R_1$), ($Q_2$, $P_2$, $W_2$, $R_2$), ($Q_3$, $P_3$, $W_3$, $R_3$), and ($Q_4$, $P_4$, $W_4$, $R_4$) represents an aromatic ring, and at least one thereof represents a pyridine ring and/or a pyrazine ring.

Above all, a phthalocyanine compound in which at least one (preferably, at least two) of rings {A ring: (A), B ring: (B), C ring: (C), and D ring: (D)} constituted of ($Q_1$, $P_1$, $W_1$, $R_1$), ($Q_2$, $P_2$, $W_2$, $R_2$), ($Q_3$, $P_3$, $W_3$, $R_3$), and ($Q_4$, $P_4$, $W_4$, $R_4$) represents an aromatic group represented by the following formula (V) is especially preferable.

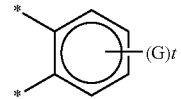

Formula (V)

In the formula (V) G represents —SO-$Z_1$, —$SO_2$-$Z_1$, —$SO_2$N$Z_1$$Z_2$, —CON$Z_1$$Z_2$, —$CO_2$$Z_1$, —CO$Z_1$, or a sulfo group.

Of these groups, —SO$_2$-Z$_1$, —SO$_2$NZ$_1$Z$_2$, and —CONZ$_1$Z$_2$ are preferable; —SO$_2$-Z$_1$, and —SO$_2$NZ$_1$Z$_2$ are more preferable; and —SO$_2$-Z$_1$ is most preferable.

Z$_1$s' may be the same or different and each represents a substituted or unsubstituted alkyl group having from 1 to 20 carbon atoms in total, a substituted or unsubstituted cycloalkyl group having from 3 to 20 carbon atoms in total, a substituted or unsubstituted alkenyl group having from 2 to 20 carbon atoms in total, a substituted or unsubstituted alkynyl group having from 2 to 12 carbon atoms in total, a substituted or unsubstituted aralkyl group having from 7 to 20 carbon atoms in total, a substituted or unsubstituted aryl group having from 6 to 20 carbon atoms in total, or a substituted or unsubstituted heterocyclic group having from 4 to 20 carbon atoms in total. Of these groups, a substituted or unsubstituted alkyl group having from 1 to 12 carbon atoms in total, a substituted or unsubstituted aryl group having from 6 to 18 carbon atoms in total, and a substituted or unsubstituted heterocyclic group having from 4 to 12 carbon atoms are preferable; and a substituted alkyl group having from 1 to 12 carbon atoms in total is most preferable.

Z$_2$s' may be the same or different and each represents a hydrogen atoms, a substituted or unsubstituted alkyl group having from 1 to 20 carbon atoms in total, a substituted or unsubstituted cycloalkyl group having from 3 to 20 carbon atoms in total, a substituted or unsubstituted alkenyl group having from 2 to 20 carbon atoms in total, a substituted or unsubstituted alkynyl group having from 2 to 12 carbon atoms in total, a substituted or unsubstituted aralkyl group having from 7 to 20 carbon atoms in total, a substituted or unsubstituted aryl group having from 6 to 20 carbon atoms in total, or a substituted or unsubstituted heterocyclic group having from 4 to 20 carbon atoms in total. Of these groups, a hydrogen atom, a substituted or unsubstituted alkyl group having from 1 to 12 carbon atoms in total, a substituted or unsubstituted aryl group having from 6 to 18 carbon atoms in total, and a substituted or unsubstituted heterocyclic group having from 4 to 12 carbon atoms are preferable; a hydrogen atom and a substituted alkyl group having from 1 to 12 carbon atoms in total are more preferable; and a hydrogen atom is most preferable.

Incidentally, Z$_1$ and/or Z$_2$ may further have a substituent such as examples enumerated above for the substituent that A$_1$ to A$_4$ can have. Z$_1$ and/or Z$_2$ has an ionically hydrophilic group as a substituent.

t represents an integer of from 0 to 4, preferably from 1 to 2, and most preferably 1.

The formula (V) is preferably represents by the following formula (V-1). In the formula (V-1), G is synonymous with that in the formula (V), and preferred examples thereof are also the same, t1 represents an integer of from 0 to 2, preferably 1 or 2, and more preferably 1.

With respect to the aromatic ring represented by the foregoing formula (V), an aromatic group represented by the following formula (VI) is especially preferable.

Formula (VI)

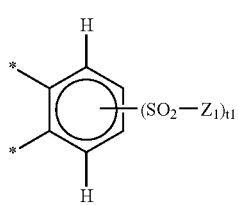

In the formula (VI) Z$_1$, t1 and * are synonymous with Z$_1$ and t in the formula (V-1), and preferred examples thereof are also the same.

As the phthalocyanine compound represented by the formula (III), the following combinations are especially preferable.

(a) A phthalocyanine compound in which at least one of rings {A ring: (A), B ring: (B), C ring: (C), and D ring: (D)} constituted of (Q$_1$, P$_1$, W$_1$, R$_1$), (Q$_2$, P$_2$, W$_2$, R$_2$), (Q$_3$, P$_3$, W$_3$, R$_3$), and (Q$_4$, P$_4$, W$_4$, R$_4$) represents a heterocyclic group is preferable.

(b) A phthalocyanine compound in which at least one of rings {A ring: (A), B ring: (B), C ring: (C), and D ring: (D)} constituted of (Q$_1$, P$_1$, W$_1$, R$_1$), (Q$_2$, P$_2$, W$_2$, R$_2$), (Q$_3$, P$_3$, W$_3$, R$_3$), and (Q$_4$, P$_4$, W$_4$, R$_4$) represents a nitrogen-containing 6-membered heterocyclic ring is preferable. However, in the case where all of the four rings represent a pyridine ring at the same time, a pyridine ring in which either one of (Q$_1$ and R$_1$), (Q$_2$ and R$_2$), (Q$_3$ and R$_3$), or (Q$_4$ and R$_4$) represents a nitrogen atom is excluded. Also, the case where all of the four rings represent a pyrazine group at the same time is excluded.

(c) A phthalocyanine compound in which at least one of rings {A ring: (A), B ring: (B), C ring: (C), and D ring: (D)} constituted of (Q$_1$, P$_1$, W$_1$, R$_1$)) (Q$_2$, P$_2$, W$_2$, R$_2$), (Q$_3$, P$_3$, W$_3$, R$_3$), and (Q$_4$, P$_4$, W$_4$, R$_4$) represents an aromatic group, and at least one thereof represents a pyridine ring or a pyrazine ring is preferable. Above all, a phthalocyanine compound in which at least one of rings {A ring: (A), B ring: (B), C ring: (C), and D ring: (D)} constituted of (Q$_1$, P$_1$, W$_1$, R$_1$), (Q$_2$, P$_2$, W$_2$, R$_2$), (Q$_3$, P$_3$, W$_3$, R$_3$), and (Q$_4$, P$_1$, W$_4$, R$_4$) represents an aromatic ring substituted with a sulfinyl group, a sulfonyl group, or a sulfamoyl group, each having an ionically hydrophilic group is more preferable; and a phthalocyanine compound in which at least one of rings {A ring: (A), B ring: (B), C ring: (C), and D ring: (D)} constituted of (Q$_1$, P$_1$, W$_1$, R$_1$), (Q$_2$, P$_2$, W$_2$, R$_2$), (Q$_3$, P$_3$, W$_3$, R$_3$), and (Q$_4$, P$_4$, W$_4$, R$_4$) represents an aromatic ring substituted with a sulfonyl group or a sulfamoyl group, each having an ionically hydrophilic group is especially preferable.

(d) M represents a hydrogen atom, a metal atom, a metal oxide, a metal hydroxide, or a metal halide; preferably Cu, Ni, Zn, or Al; and most preferably Cu.

(e) The phthalocyanine compound preferably has a molecular weight (average) in the range of from 995 to 2,500 more preferably from 995 to 2,000, further preferably from 995 to 1,800, and most preferably from 995 to 1,600.

(f) The ionically hydrophilic group that the phthalocyanine compound represented by the formula (III) has in one molecule thereof is preferably a sulfo group, a carboxyl group, or a phosphono group, and especially preferably a sulfo group. The sulfo group, the carboxyl group, and the phosphono group may be each in the state of a salt. Examples of counter ions capable of forming a salt include an ammonium ion, an alkali metal ion (such as a lithium ion, a sodium ion, and a potassium ion), and an organic cation (such as a tetramethylammonium ion, a tetramethylguanidium ion, and a tetramethylphosphonium ion). Of the counter ions, an alkali metal salt is preferable. A lithium salt is especially preferable because it can enhance the solubility of the compound and improve the ink stability.

With respect to the phthalocyanine compound represented by the formula (III), those having at least one ionically hydrophilic group in one molecule thereof are preferable, and those in which the ionically hydrophilic group is a sulfo group are more preferable. Above all, those having two or more sulfo group as the ionically hydrophilic group are most preferable.

Since the phthalocyanine compound represented by the formula (III) has at least one ionically hydrophilic group in the molecule thereof, its solubility or dispersibility in an aqueous medium is good.

The phthalocyanine compound represented by the formula (I), (II) or (III) according to the invention is a novel water-soluble compound having a specific structure (especially, one in which the benzene ring as the phthalocyanine mother nucleus is substituted with a heterocyclic ring and/or an aromatic ring substituted with a specific substituent), is useful as an inkjet water-soluble dye and an intermediate for synthesizing the water-soluble dye, and is a compound that can be an intermediate for chemical, medical or agricultural organic compounds.

The phthalocyanine compound represented by the formula (III) according to the invention can be derived by reacting a dicarbonitrile derivative (Compound a represented by formula a) and/or a 1,3-diiminoisoindoline derivative (Compound b represented by formula b) with a metal derivative represented by the formula (VII) in the following reaction scheme. The synthesis of the water-soluble substituted phthalocyanine compound includes a method in which Compound a and/or Compound b in which an ionically hydrophilic group has been introduced in advance is used as a starting material and a method in which after obtaining the phthalocyanine compound, an ionically hydrophilic group is introduced thereinto, thereby making it soluble in water.

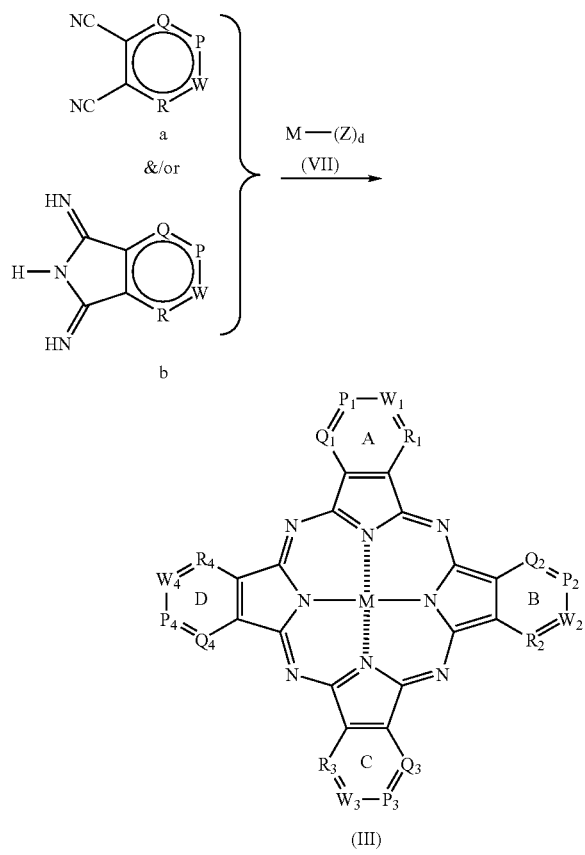

(III)

In the foregoing reaction scheme, Q, P, W, and R are respectively corresponding to $Q_1$ to $Q_4$, $P_1$ to $P_4$, $W_1$ to $W_4$, and $R_1$ to $R_4$ in the foregoing formula (III).

In the case at least one of the A ring, the B ring, the C ring and the D ring in the phthalocyanine compound represented by the formula (III) is a heterocyclic ring (especially preferably, a nitrogen-containing heterocyclic ring) and at least one of the A ring, the B ring, the C ring and the D ring in the substituted phthalocyanine compound represented by the formula (III) is an aromatic ring, the phthalocyanine compound represented by the formula (III) can be produced, for example, from raw materials those are the dicarbonitrile derivative (Compound a) and/or the 1,3-diiminoisoindoline derivative (Compound b) wherein the ring of Q, P, W and R form a heterocyclic ring (especially preferably, a nitrogen-containing heterocyclic ring) and the dicarbonitrile derivative (Compound a) and/or the 1,3-diiminoisoindoline derivative (Compound b) wherein the ring of Q, P, W and R form an aromatic ring.

In the production process of the phthalocyanine compound represented by the formula (I), (II) or (III) according to the invention, the conditions of the reaction between the dicarbonitrile derivative (Compound a) and/or the 1,3-diiminoisoindoline derivative (Compound b) and the metal derivative represented by the formula (VII) according to the foregoing reaction scheme will be described below in detail.

The acid that is used in the invention is not particularly limited, but any of organic compounds and inorganic compounds having a dissociation index pKa in aqueous solution of not more than 7.0 at 25° C. are preferable. The pKa is a logarithmic value of an inverse of acid dissociation constant and is a value determined at an ionic strength of 0.1 at 25° C. As the acid having a pKa of from 0.0 to 7.0, any of inorganic acids such as phosphoric acid and organic acids such as acetic acid, malonic acid, and citric acid are employable, but the acid having a pKa of from 0.0 to 7.0 and exhibiting an effect by the foregoing improvement is an organic acid. Also, a carboxyl group-containing organic acid is most preferable among the organic acids. The organic acid having a pKa of from 0.0 to 7.0 may be a monobasic organic acid or a polybasic organic acid. In the case of a polybasic organic acid, it can be used as a metal salt (such as a sodium salt and a potassium salt) or an ammonium salt so far as the pKa falls within the foregoing range of from 0.0 to 7.0. Also, the organic acid having a pKa of from 0.0 to 7.0 can be used in admixture of two or more thereof. Preferred examples of the organic acid having a pKa of from 0.0 to 7.0 that is used in the invention include a variety of organic acids such as aliphatic monobasic organic acids such as formic acid, acetic acid, monochloroacetic acid, monobromoacetic acid, glycolic acid, propionic acid, monochloropropionic acid, lactic acid, pyruvic acid, acrylic acid, butyric acid, isobutyric acid, pivalic acid, aminobutyric acid, valeric acid, and isovaleric acid; amino acid based compounds such as asparagine, alanine, alginine, ethionine, glycine, glutamine, cysteine, serine, methionine, and leucine; aromatic monobasic organic acids such as benzoic acid, chloro- or hydroxy-mono-substituted benzoic acid, and nicotinic acid; aliphatic dibasic organic acids such as oxalic acid, malonic acid, succinic acid, tartaric acid, malic acid, maleic acid, fumaric acid, oxaloacetic acid, glutaric acid, and adipic acid; amino acid based dibasic organic acids such as aspartic acid, glutamic acid, cystine, and ascorbic acid; aromatic dibasic organic acids such as phthalic acid and terephthalic acid; and tribasic organic acids such as citric acid. In the invention, of these organic acids, aliphatic monobasic organic acids are preferable, and formic acid, acetic acid, and propionic acid are most preferable.

When the compound having a pKa of not more than 7.0 is used and charged in an amount of from 0.05 to 20 times, and preferably from 0.1 to 10 times the amount of the dicarbonitrile derivative (Compound a) and/or the 1,3-diiminoisoindoline derivative (Compound b) to be used, a decomposition inhibition action of the dicarbonitrile derivative (Compound a) and/or the 1,3-diiminoisoindoline derivative (Compound b) is obtained. When the amount of the acid having a pKa of not more than 7.0 to be used is less than 0.05 times the amount of the dicarbonitrile derivative (Compound a) and/or the 1,3-diiminoisoindoline derivative (Compound b) to be used, it is insufficient to inhibit the decomposition of the dicarbonitrile derivative (Compound a) and/or the 1,3-diiminoisoindoline derivative (Compound b). On the other hand, in the case where the amount of the acid having a pKa of not more than 7.0 to be used exceeds 20 times the amount of the dicarbonitrile derivative (Compound a) and/or the 1,3-diiminoisoindoline derivative (Compound b) to be used, since the reaction system is deviated into the acidic side, the reaction hardly proceeds. Also, since the base is excessively used until the mixture becomes the buffer solution, a salt between the acid and the base may possibly be generated as a crystal.

The base that can be used in the present reaction is an inorganic base or an organic base. Examples of the inorganic base that can be used include lithium carbonate, sodium carbonate, potassium carbonate, sodium hydrogencarbonate, lithium hydroxide, and potassium hydroxide; and examples of the organic base that can be used include triethylamine, tributylamine, diisopropylethylamine, pyridine, and dimethylaminopyridine. Besides, organic acid salts such as lithium acetate, potassium acetate, sodium oxalate, and disodium ethylenediaminetetraacetate can also be used. However, since such a base is dissolved in a reaction solvent to serve as a buffer solution, bases having high solubility are preferable, and organic bases and organic acid salts composed of an alkaline metal ion are most preferable. Of alkali metal ions, a lithium ion, a sodium ion, and a potassium ion are preferable. Especially, organic acid salts of a lithium ion or a sodium ion are most preferable. The base is used in an amount of from 0.05 to 30.0 equivalents, and preferably from 0.5 to 15.0 equivalents to the amount of the dicarbonitrile derivative (Compound a) and/or the 1,3-diiminoisoindoline derivative (Compound b) to be used.

A buffer solution as referred to herein is a solution having a large buffer action against the changes in concentrations of components in the solution. For example, a mixed solution of a weak acid (AH) such as acetic acid and a conjugated base thereof (A$^-$) can suppress the pH change with a slight range even by adding a small amount of H$^+$ or OH$^-$. A system containing a weak base (B) and a conjugated acid thereof (BH$^+$) also exhibits the same action. Practically useful pH buffer solutions are found in many books, and the details are described in, for example, *Rikagakujiten* (Dictionary of Physics and Chemistry), 5th Edition, edited by Saburo Nagakura and published by Iwanami Shoten (1999).

In the production process of the phthalocyanine compound according to the invention, it is preferable to react the dicarbonitrile derivative (Compound a) and/or the 1,3-diiminoisoindoline derivative (Compound b) with the metal derivative represented by the foregoing formula (VII) in the presence of the acid having a pKa of not more than 7.0. With respect to the reaction conditions, the reaction temperature is from 30 to 220° C., preferably from 40 to 200° C., and more preferably from 50 to 180° C. In the case where the reaction temperature is lower than 30° C., the reaction rate becomes remarkably slow, and it takes an extremely long period of time for the synthesis, and hence, such is not economical. On the other hand, in the case of synthesis at a high temperature exceeding 220° C., the amount of by-products increases, and hence, such is not preferable, too.

As the metal derivative represented by the formula (VII) that is added in the reaction of the invention, not only a metal that is intended to be introduced, a metal against the metal oxide, and a metal hydroxide, but also a metal chloride, a metal acetate, and an aquocomplex or ammnine complex of a metal as a complex can be used.

In the formula (VII), M is preferably a metal atom or its oxide, hydroxide or halide.

Examples the metal atom include Li, Na, K, Mg, Ti, Zr, V, Nb, Ta, Cr, Mo, W, Mn, Fe, Co, Ni, Ru, Rh, Pd, Os, Ir, Pt, Cu, Ag, Au, Zn, Cd, Hg, Al, Ga, In, Si, Ge, Sn, Pb, Sb, and Bi.

Examples of the oxide include VO and GeO.

Examples of the hydroxide include $Si(OH)_2$, $Cr(OH)_2$, and $Sn(OH)_2$.

Examples of the halide include $AlCl$, $SiCl_2$, $VCl$, $VCl_2$, $COCl$, $FeCl$, $GaCl$, and $ZrCl$.

Above all, M is preferably Cu, Ni, Zn, or Al, and most preferably Cu.

In the formula (VII), Z represents a monovalent or divalent ligand such as a halogen atom, an acetic acid anion, acetyl acetonate, and oxygen; and d represents an integer of from 1 to 4.

Specific examples of the metal derivative {metal derivative represented by the formula (VII)} include halides, carboxylic acid derivatives, sulfuric acid salts, nitric acid salts, carbonyl compounds, oxides, and complexes of Al, Si, Ti, V, Mn, Fe, Co, Ni, Cu, Zn, Ge, Ru, Rh, Pd, In, Sn, Pt, Pb, etc. More specifically, there are enumerated copper chloride, copper bromide, copper iodide, copper acetate, nickel chloride, nickel bromide, nickel acetate, cobalt chloride, cobalt bromide, cobalt acetate, iron chloride, zinc chloride, zinc bromide, zinc iodide, zinc acetate, vanadium chloride, vanadium oxytrichloride, palladium chloride, palladium acetate, aluminum chloride, manganese chloride, manganese acetate, manganese acetylacetone, manganese chloride, lead chloride, lead acetate, indium chloride, titanium chloride, and tin chloride.

Of these, cupric chloride ($CuCl_2$) and copper acetate are especially preferable, and cupric chloride ($CuCl_2$) is most preferable.

The metal derivative is preferably used in an amount of from 0.01 to 10 equivalents, more preferably from 0.05 to 5 equivalents, and especially preferably from 0.1 to 3 equivalent to the amount of the dicarbonitrile derivative (Compound a) and/or the 1,3-diiminoisoindoline derivative (Compound b) to be used.

Also, in the invention, a catalyst may be used at the same time. In the invention, as the catalyst, all catalysts that are usually used in the synthesis of phthalocyanine compounds can be used. Examples include molybdenum compounds such as ammonium molybdate, molybdnic acid, ammonium phosphomolybdate, and molybdenum oxide; tungsten compounds such as ammonium tungstate and ammonium phosphotungstate; arsenic vanadium compounds; boric acid; and halides or oxyhalides of titanium, tin, and antimony. Of these compounds, ammonium molybdate is excellent.

As the solvent that is used in the process of the invention, general organic solvents can be used. Of these solvents, hydroxyl group-containing organic solvents and polar solvents (such as acetonitrile, formamide, N,N-dimethylformamide, N,N-dimethylacetamide, dimethyl sulfoxide, sulfolane, propylene carbonate, N-methyl-2-pyrrolidone, N-vinyl-2-pyrrolidone, and N,N-diethyldodecanamide) are preferable. More preferred examples of alcohols include methanol, ethanol, n-propanol, isopropanol, n-pentanol, n-heptanol, n-octanol, cyclohexanol, benzyl alcohol, phenethyl alcohol, phenylpropyl alcohol, furfuryl alcohol, and anise alcohol. Also, mono- and oligo- (especially, di- and tri-) and poly-$C_2$–$C_4$-alkylene glycols (simply referred to as "glycol") and their mono-$C_1$–$C_8$-alkyl- and monoaryl ethers (simply referred to as "glycol monoether") are suitable. Compounds containing ethylene as a basis are also advantageous. Examples include ethylene glycol, 1,2-propylene glycol, 1,3-propylene glycol, diethylene glycol, butylene glycol, triethylene glycol, tetraethylene glycol, diproplylene glycol, tripropylene glycol, tetrapropylene glycol, polyethylene glycol, polypropylene glycol, ethylene glycol monomethyl ether, ethylene glycol monoethyl ether, ethylene glycol monopropyl ether, ethylene glycol monobutyl ether, ethylene glycol monohexyl ether, propylene glycol monomethyl ether, propylene glycol monoethyl ether, propylene glycol monopropyl ether, propylene glycol monobutyl ether, propylene glycol monohexyl ether, diethylene glycol monomethyl ether, triethylene glycol monomethyl ether, tetraethylene glycol monomethyl ether, diethylene glycol monoethyl ether, triethylene glycol monoethyl ether, tetraethylene glycol monoethyl ether, diethylene glycol monobutyl ether, triethylene glycol monobutyl ether, tetraethylene glycol monobutyl ether, dipropylene glycol monomethyl ether, tripropylene glycol monomethyl ether, tetrapropylene glycol monomethyl ether, dipropylene glycol monoethyl ether, tripropylene glycol monoethyl ether, tetrapropylene glycol monoethyl ether, dipropylene glycol monobutyl ether, tripropylene glycol monobutyl ether, tetrapropylene glycol monobutyl ether, ethylene glycol monophenyl ether, and propylene glycol monophenyl ether. Of these alcohols, methanol, ethanol, isopropanol, ethylene glycol, 1,2-propylene glycol, 1,3-propylene glycol, diethylene glycol, triethylene glycol, tetraethylene glycol, dipropylene glycol, tripropylene glycol, and tetrapropylene glycol are preferable; and ethylene glycol and diethylene glycol are most preferable.

Also, in the invention, inert solvents that are industrially used can be used. Examples include nitrobenzene, trichlorobenzene, chloronaphthalene, methylnaphthalene, naphthalene, alkylbenzenes, paraffins, naphthenes, kerosene.

The inert solvent may be used singly or in admixture of two or more thereof so far as no influence is given. The solvent is used in an amount of from 1 to 100 times by weight, preferably from 1 to 20 times by weight, and more preferably from 1 to 5 times by weight the amount of the dicarbonitrile derivative (Compound a) and/or the 1,3-diiminoisoindoline derivative (Compound b) to be used.

In the present reaction, what the reaction is carried out for a long period of time may possibly adversely affect the stability of the desired product or cause side-reactions and is not economy. The reaction time is preferably shorter than 10 hours, more preferably shorter than 8 hours, and further preferably shorter than 6 hours.

In the production process of the phthalocyanine compound of the invention, the product (phthalocyanine compound) obtained by these reactions is treated according to the post treatment to be carried out in usual organic synthesis reactions and can be then provided with or without being purified.

That is, for example, the product liberated from the reaction system can be provided without being purified or through a purification operation such as recrystallization and column chromatography (for example, gel permeation chromatography (SEPHADEX™ LH-20, manufactured by Pharmacia)) singly or jointly.

Also, after completion of the reaction, the product is poured into water or ice with or without distillation of the reaction solvent, liberated with or without being neutralized, and then purified through an operation such as recrystallization and column chromatography singly or jointly, and the purified product can be provided.

Also, after completion of the reaction, the product is poured into water or ice with or without distillation of the reaction solvent and extracted with an organic solvent/aqueous solution with or without being neutralized, and the extracted product can be provided without being purified or through a purification operation such as recrystallization and column chromatography singly or jointly.

In summary, the production process of the phthalocyanine compound of the invention is preferably a production process comprising a combination of the following (a) to (f).

(a) The acid that is used in the invention is not particularly limited, but any of organic compounds and inorganic compounds are preferable so far as an acid or conjugated acid in an aqueous solution has a dissociation index pKa of not more than 7.0 at 25° C. Of these acids, organic acids having a pKa of from 0.0 to 7.0 are preferable, and carboxyl group-containing organic acids are most preferable. Of the organic acids, aliphatic monobasic organic acids are preferable, and formic acid, acetic acid, and propionic acid are most preferable.

(b) As the base, inorganic bases comprising an alkali metal or organic bases can be used. Examples of the inorganic bases include lithium carbonate, sodium carbonate, potassium carbonate, sodium hydrogencarbonate, lithium hydroxide, and potassium hydroxide; and examples of the organic bases include triethylamine, tributylamine, diisopropylethylamine, pyridine, and dimethylaminopyridine. Besides, lithium acetate, potassium acetate, sodium oxalate, and disodium ethylenediaminetetraacetate can be used.

(c) With respect to the reaction conditions, the reaction temperature is from 30 to 220° C., preferably from 40 to 200° C., and especially preferably from 50 to 180° C.

(d) As the metal or metal oxide that can be introduced, VO, TiO, Mn, Fe, Co, Ni, Cu, Zn, Pd, Cd, and Mg can be enumerated. Of these, Ni, Cu, and Zn are preferable. As the state of salt, chlorides and acetates are especially preferable. The use amount is from 0.1 to 3 equivalents to the amount of the dicarbonitrile derivative (Compound a) and/or the 1,3-diiminoisoindoline derivative (Compound b) to be used.

(e) As the solvent, methanol, ethanol, isopropanol, ethylene glycol, and diethylene glycol are most preferable. The solvent is used in an amount of from 1 to 5 times by weight the amount of the dicarbonitrile derivative (Compound a) and/or the 1,3-diiminoisoindoline derivative (Compound b) to be used.

(f) The reaction time is especially preferably shorter than 6 hours.

The correlation between the structure and the performance of the phthalocyanine compound of the invention will be described below while dividing into (1) the oxidation potential of the substituted phthalocyanine compound to be used in an image forming ink and (2) the structural characteristic of the substituted phthalocyanine compound.

(1) Oxidation Potential of Substituted Phthalocyanine Compound:

In the production process of the phthalocyanine compound of the invention, by choosing a substituent having large electron withdrawing properties as the soluble group or substituent, it is possible to make the oxidation potential of the resulting phthalocyanine dye high (noble) and to further suppress the reactivity with active gases (for example, oxidizing gases) such as ozone and singlet oxygen. Thus, pigments having resistance to active gases can be obtained.

All of the phthalocyanine compounds of the invention have an oxidation potential of nobler than 1.0 V (vs SCE). As a result, it has been found that it is very important to have this physical property value for the sake of improving the fastness of the formed image.

That is, this matter is an extremely important structural characteristic (to control the oxidation potential of the phthalocyanine dye mixture) as a measure of achieving improvements in preservability of the formed image (such as resistance to light and resistance to ozone gas) as one of the objects of the invention.

In the present specification, the term "resistance to ozone gas" as referred to herein stands for resistance to ozone gas and includes resistance to oxidizing atmospheres other than ozone gas, too. That is, the phthalocyanine compound represented by the formula (I) according to the invention is characterized in that it has strong resistance to oxidizing gases present in the general environment, such as nitrogen oxides often found in exhaust gases in automobiles, sulfur oxides often found in exhausts from thermal power plants and factories, photochemical smog rich in ozone gas, oxygen-nitrogen radicals, and oxygen-hydrogen radicals generated by photochemical radical chain reaction of these oxides by sunlight, and hydrogen peroxide radicals generated from a place where a special chemical solution is used, such as beauty parlors. Accordingly, in the case where oxidative degradation of images such as outdoor advertisements and guidance in railroad facilities constrains the image life, by using the phthalocyanine compound according to the invention as an image forming material, it is possible to improve resistance to oxidizing atmospheres, i.e., so called ozone gas resistance.

(2) Ink Stability with Time of Phthalocyanine Compound:

With respect to phthalocyanine compounds, hue, fastness, crystallinity, and storage stability were reviewed. As a result, it has been found that by using a substituted phthalocyanine compound in which at least one specific substituent is introduced at a specific substitution position {for example, a sulfonyl group is introduced in at least one portion of the four aromatic rings of a phthalocyanine mother nucleus}, and at least specific substituent {at least one of the four rings of a phthalocyanine mother nucleus is a nitrogen-containing 6-membered heterocyclic ring} is incorporated, the foregoing problems can be solved, whereby all of good hue, image fastness and long-term stability with time of an ink solution can be realized at the same time.

In detail, it is considered that the foregoing requirements can be achieved by the substituted phthalocyanine compound of the invention having (1) a good spectral absorption characteristic (the dicarbonitrile derivative (Compound a) and/or the 1,3-diiminoisoindoline derivative (Compound b) is used as the main starting material), (2) high image fastness (high oxidation potential; by introducing a sulfonyl group, a sulfamoyl group, or a nitrogen-containing heterocyclic ring, for example, color fading by oxidation reaction between the substituted phthalocyanine compound and ozone gas as a nucleophilic reagent is suppressed), (3) high solubility in the ink composition, and (4) giving of good stability with time of ink solution, in which the specific number of specific soluble groups can be introduced at specific substitution positions (in a optimal mixing ratio of at least one dicarbonitrile derivative (Compound a) and/or 1,3-diiminoisoindoline derivative (Compound b)).

The improving effects in hue, light fastness, ozone gas resistance, etc. and giving of characteristics required in the ink (coloring composition), which are brought by the structural characteristics of the specific substituents, are quite unpredictable from the conventional technologies as described previously.

Specific examples (Dyes 101 to 125) of the phthalocyanine compound represented by the formula (III) according to the invention will be given below, but it should not be construed that the invention is limited to these specific examples.

In the following tables, the examples of the four rings (A), (B), (C) and (D) of the phthalocyanine mother nucleus are derived from a charging ratio (eq./eq.) of raw materials ,having different structures, of the dicarbonitrile derivative (Compound a) and/or the 1,3-diiminoisoindoline derivative (Compound b) at the time of condensation reaction during the synthesis of the substituted phthalocyanine compound of the invention, which represents an average value of the mixing ratio of the resulting substituted phthalocyanine compound.

TABLE 1

| Illustrative Compound | M | (A) | (B) | (C) | (D) |
|---|---|---|---|---|---|
| 101 | Cu | [structure with SO$_2$(CH$_2$)$_3$SO$_3$Li] | [structure with SO$_2$(CH$_2$)$_3$SO$_3$Li] | [structure with SO$_2$(CH$_2$)$_3$SO$_3$Li] | [pyridine structure] |

TABLE 1-continued

| Illustrative Compound | M | (A) | (B) | (C) | (D) |
|---|---|---|---|---|---|
| 102 | Cu | 3,4,5-trimethylphenyl-SO$_2$(CH$_2$)$_3$SO$_3$Li | 3,4,5-trimethylphenyl-SO$_2$(CH$_2$)$_3$SO$_3$Li | 3,4,5-trimethylphenyl-SO$_2$(CH$_2$)$_3$SO$_3$Li | 3,4-dimethylpyridine |
| 103 | Cu | 3,4,5-trimethylphenyl-SO$_2$(CH$_2$)$_3$SO$_3$Li | 3,4,5-trimethylphenyl-SO$_2$(CH$_2$)$_3$SO$_3$Li | 3,4,5-trimethylphenyl-SO$_2$(CH$_2$)$_3$SO$_3$Li | 3,4-dimethylpyrazine |
| 104 | Cu | 3,4,5-trimethylphenyl-SO$_2$(CH$_2$)$_3$SO$_3$Li | 3,4,5-trimethylphenyl-SO$_2$(CH$_2$)$_3$SO$_3$Li | 2,3-dimethylpyridine | 2,3-dimethylpyridine |
| 105 | Cu | 3,4,5-trimethylphenyl-SO$_2$(CH$_2$)$_3$SO$_3$Li | 3,4,5-trimethylphenyl-SO$_2$(CH$_2$)$_3$SO$_3$Li | 3,4-dimethylpyridine | 3,4-dimethylpyridine |

TABLE 2

| Illustrative Compound | M | (A) | (B) | (C) | (D) |
|---|---|---|---|---|---|
| 106 | Cu | 3,4,5-trimethyl-phenyl-di(SO$_2$(CH$_2$)$_3$SO$_3$Li) | 3,4,5-trimethyl-phenyl-di(SO$_2$(CH$_2$)$_3$SO$_3$Li) | 3,4,5-trimethyl-phenyl-di(SO$_2$(CH$_2$)$_3$SO$_3$Li) | 2,3-dimethylpyridine |
| 107 | Cu | 3,4,5-trimethyl-phenyl-di(SO$_2$(CH$_2$)$_3$SO$_3$Li) | 3,4,5-trimethyl-phenyl-di(SO$_2$(CH$_2$)$_3$SO$_3$Li) | 3,4,5-trimethyl-phenyl-di(SO$_2$(CH$_2$)$_3$SO$_3$Li) | 3,4-dimethylpyridine |

TABLE 2-continued

| Illustrative Compound | M | (A) | (B) | (C) | (D) |
|---|---|---|---|---|---|
| 108 | Cu | phenyl with H, H, and two SO₂(CH₂)₃SO₃Li groups | phenyl with H, H, and two SO₂(CH₂)₃SO₃Li groups | phenyl with H, H, and two SO₂(CH₂)₃SO₃Li groups | 2,3-dimethylpyrazine |
| 109 | Cu | phenyl with H, H, and two SO₂(CH₂)₃SO₃Li groups | phenyl with H, H, and two SO₂(CH₂)₃SO₃Li groups | 2,3-dimethylpyridine | 3,4-dimethylpyridine |
| 110 | Cu | phenyl with H, H, and two SO₂(CH₂)₃SO₃Li groups | 2,3-dimethylpyrazine | 2,3-dimethylpyridine | 3,4-dimethylpyridine |

TABLE 3

| Illustrative Compound | M | (A) | (B) |
|---|---|---|---|
| 111 | Cu | phenyl with H, H and SO₂(CH₂)₃SO₃Li | phenyl with H, H and SO₂(CH₂)₃SO₃Li |
| 112 | Cu | phenyl with H, H and two SO₂(CH₂)₃SO₃Li | phenyl with H, H and SO₂(CH₂)₃SO₃Li |
| 113 | Cu | phenyl with H, H and SO₂(CH₂)₃SO₂NHCH₂CH(OH)CH₂SO₃Li | phenyl with H, H and SO₂(CH₂)₃SO₂NHCH₂CH(OH)CH₂SO₃Li |

TABLE 3-continued

| | | (C) | |
|---|---|---|---|
| 114 | Cu | phenyl(H,H)-SO$_2$(CH$_2$)$_3$CO$_2$Li | phenyl(H,H)-SO$_2$(CH$_2$)$_3$CO$_2$Li |
| 115 | Cu | phenyl(H,H)-SO$_2$CH$_2$CH$_2$CH(CH$_3$)SO$_3$Li | phenyl(H,H)-SO$_2$CH$_2$CH$_2$CH(CH$_3$)SO$_3$Li |

| Illustrative Compound | M | (C) | (D) |
|---|---|---|---|
| 111 | Cu | phenyl(H,H)-SO$_2$(CH$_2$)$_3$SO$_2$NHCH$_2$CH(OH)CH$_3$ | 2,3-dimethylpyridine |
| 112 | Cu | phenyl(H,H)-SO$_2$(CH$_2$)$_3$SO$_3$Li | 3,4-dimethylpyridine |
| 113 | Cu | phenyl(H,H)-SO$_2$(CH$_2$)$_3$SO$_2$NHCH$_2$CH(OH)CH$_2$SO$_3$Li | 2,3-dimethylpyridine |
| 114 | Cu | phenyl(H,H)-SO$_2$(CH$_2$)$_3$CO$_2$Li | 2,3-dimethylpyrazine |
| 115 | Cu | phenyl(H,H)-SO$_2$CH$_2$CH$_2$CH(CH$_3$)SO$_3$Li | 3,4-dimethylpyridine |

TABLE 4

| Illustrative Compound | M | (A) | (B) | (C) | (D) |
|---|---|---|---|---|---|
| 116 | Cu | 3,4-dimethylphenyl-SO₂NH(CH₂)₂SO₃Li | 3,4-dimethylphenyl-SO₂NH(CH₂)₂SO₃Li | 3,4-dimethylphenyl-SO₂NH(CH₂)₂SO₃Li | 2,3-dimethylpyridine |
| 117 | Ni | 3,4-dimethylphenyl-SO₂NH(CH₂)₃SO₃Li | 3,4-dimethylphenyl-SO₂NH(CH₂)₃SO₃Li | 3,4-dimethylphenyl-SO₂NH(CH₂)₃SO₃Li | 3,4-dimethylpyridine |
| 118 | Zn | 3,4-dimethylphenyl-SO₂NH(CH₂)₂SO₃Li | 3,4-dimethylphenyl-SO₂NH(CH₂)₂SO₃Li | 3,4-dimethylphenyl-SO₂NH(CH₂)₂SO₃Li | 2,3-dimethylpyrazine |
| 119 | Cu | 3,4-dimethylphenyl-CONH(CH₂)₂SO₃Li | 3,4-dimethylphenyl-CONH(CH₂)₂SO₃Li | 3,4-dimethylphenyl-CONH(CH₂)₂SO₃Li | 2,3-dimethylpyridine |
| 120 | Cu | 3,4-dimethylphenyl-SO₂(CH₂)₃SO₃Li | 3,4-dimethylphenyl-SO₂NH(CH₂)₂SO₃Li | 2,3-dimethylpyridine | 2,3-dimethylpyridine |

TABLE 5

| Illustrative Compound | M | (A) | (B) | (C) | (D) |
|---|---|---|---|---|---|
| 121 | Cu | 4,5-dimethyl-1-((CH₂)₃SO₃K)imidazole | 4,5-dimethyl-1-((CH₂)₃SO₃K)imidazole | 4,5-dimethyl-1-((CH₂)₃SO₃K)imidazole | 4,5-dimethyl-1-((CH₂)₃SO₃K)imidazole |
| 122 | Cu | 2,3-dimethylbenzothiophene-SO₃Li | 2,3-dimethylbenzothiophene-SO₃Li | 2,3-dimethylbenzothiophene-SO₃Li | 2,3-dimethylbenzothiophene-SO₃Li |

TABLE 5-continued

| Illustrative Compound | M | (A) | (B) | (C) | (D) |
|---|---|---|---|---|---|
| 123 | Cu | [structure with S(CH$_2$)$_3$SO$_3$Na] | [structure with S(CH$_2$)$_3$SO$_3$Na] | [structure with S(CH$_2$)$_3$SO$_3$Na] | [structure with S(CH$_2$)$_3$SO$_3$Na] |
| 124 | Cu | [structure with CH$_2$CO$_2$K and CN] | [structure with CH$_2$CO$_2$K and CN] | [structure with CH$_2$CO$_2$K and CN] | [structure with CH$_2$CO$_2$K and CN] |
| 125 | Cu | [structure with (CH$_2$)$_3$SO$_3$Li] | [structure with (CH$_2$)$_3$SO$_3$Li] | [structure with (CH$_2$)$_3$SO$_3$Li] | [structure with (CH$_2$)$_3$SO$_3$Li] |

Conventionally, the phthalocyanine compounds are used as a mixture of isomers in which the position into which a specific substituent is introduced is different (the number of substituents to be introduced is different as the case may be). On the other hand, the compound of the invention (the compound represented by the formula (I), (II) or (III), i.e., the substituted phthalocyanine compound having a specific structure in which the specific number of specific substituents are selectively introduced at specific positions) is a novel compound having a specific structure, which has not been separated and recognized so far. The performance to be brought by the specific structure is extremely useful as an inkjet dye having high functionality imparted thereto and an intermediate for synthesizing the dye.

In more detail, the phthalocyanine compound (or mixture) of the invention can be applied as, for example, a material for forming an image, especially a color image. Concretely, examples of the application include a recording material (ink) for inkjet recording, a heat-sensitive transfer type image recording material, a pressure-sensitive recording material, a recording material using an electrophotographic mode, a transfer type silver halide photosensitive material, a printing ink, and a recording pen. Above all, a recording material (ink) for inkjet recording, a heat-sensitive transfer type image recording material, and a recording material using an electrophotographic mode are preferable, and a recording material (ink) for inkjet recording is more preferable. Also, the phthalocyanine compound of the invention can be applied to a color filter to be used in solid imagers such as LCD and CCD as described in U.S. Pat. No. 4,808,501 and JP-A-6-35182 and to a dyeing solution for dyeing a variety of fibers. The phthalocyanine compound of the invention can be used upon adjusting physical properties such as solubility and heat transfer properties by the substituent so as to adapt to the application.

[Inkjet Recording Ink]

Next, the inkjet recording ink of the invention will be described below.

An inkjet recording ink can be prepared by dissolving and/or dispersing the phthalocyanine compound (or mixture) in an oleophilic medium or an aqueous medium. Above all, an ink using an aqueous medium is preferable.

If desired, the ink can contain other additives within the range wherein the effects of the invention are not hindered. Examples of other additives include known additives such as a drying preventive (wetting agent), a color fading preventive, an emulsion stabilizer, a penetration accelerator, an ultraviolet absorber, an antiseptic, a fungicide, a pH adjustor, a surface tension adjustor, an antifoaming agent, a viscosity adjustor, a dispersant, a dispersion stabilizer, a rust preventive, and a chelating agent. In the case of an aqueous ink, these various additives are directly added to an ink liquid. In the case of using an oleophilic dye in the form of a dispersion, it is general to add the additives to a dispersion after preparing a dye dispersion, but the additives may be added to an oil phase or an aqueous phase at the time of preparation.

The drying inhibitor is suitably used for the purpose of preventing clogging of an ink jet head of nozzle to be used in the inkjet recording mode, which occurs upon drying of the inkjet ink.

As the drying preventive, water-soluble organic solvents having a vapor pressure lower than water are preferable. Specific examples include polyhydric alcohols represented by ethylene glycol, propylene glycol, diethylene glycol, polyethylene glycol, thiodiglycol, dithiodiglycol, 2-methyl-1,3-propanediol, 1,2,6-hexanetriol, acetylene glycol derivatives, glycerin, trimethylolpropane, etc.; lower alkyl ethers of polyhydric alcohol such as ethylene glycol monomethyl ether, ethylene glycol monoethyl ether, diethylene glycol monomethyl ether, diethylene glycol monoethyl ether, triethylene glycol monoethyl ether, and triethylene glycol monobutyl ether; heterocyclic compounds such as 2-pyrrolidone, N-methyl-2-pyrrolidone, 1,3-dimethyl-2-imidazolidinone, and N-ethylmorpholine; sulfur-containing compounds such as sulfolane, dimethyl sulfoxide, and 3-sulfolene; polyfunctional compounds such as diacetone alcohol and diethanolamine; and urea derivatives of these compounds, polyhydric alcohols such as glycerin and diethylene glycol are preferable. The drying preventive may be used singly or in admixture of two or more thereof. It is preferable that the drying preventive is contained in an amount of from 10 to 50% by weight in the ink.

The penetration accelerator is suitably used for the purpose of better penetrating the inkjet ink into paper. Examples of the penetration accelerator include alcohols such as ethanol, isopropanol, butanol, diethylene glycol monobutyl ether, triethylene glycol monobutyl ether, and 1,2-hexanediol; and nonionic surfactants such as sodium lauryl sulfate and sodium oleate. When the penetration accelerator is contained in an amount of from 5 to 30% by weight in the ink, the effect is usually revealed sufficiently. It is preferable to use the penetration accelerator within the range of an addition amount in which bleeding of prints or print-through does not occur.

The ultraviolet absorber is used for the purpose of improving the preservability of an image. As the ultraviolet absorber, benzotriazole based compounds described in JP-A-58-185677, JP-A-61-190537, JP-A-2-782, JP-A-5-197075, JP-A-9-34057, etc.; benzophenone based compounds described in JP-A-46-2784, JP-A-5-194483, U.S. Pat. No. 3,214,463, etc.; cinnamic acid based compounds described in JP-B-48-30492, JP-B-56-21141, JP-A-10-88106, etc.; triazine based compounds described in JP-A-4-298503, JP-A-8-53427, JP-A-8-239368, JP-A-10-182621, JP-T-8-501291, etc.; and compounds described in *Research Disclosure*, No. 24239 can be used. So-called fluorescent brighteners as a compound that absorbs a ultraviolet light to emit fluorescence, represented by stilbene based compounds and benzoxazole based compounds, can also be used.

The color fading preventive is used for the purpose of improving the preservability of an image. As the color fading preventive, a variety of organic or metal complex based color fading preventives can be used. Examples of organic color fading preventives include hydroquinones, alkoxyphenols, dialkoxyphenols, phenols, anilines, amines, indanes, chromans, alkoxyanilines, and heterocyclic compounds; and examples of metal complexes include nickel complexes and zinc complexes. More specifically, compounds described in patents cited in *Research Disclosure*, No. 17643, VII-I to VII-J, *Research Disclosure*, No. 15162, *Research Disclosure*, No. 18716, page 650, left column, *Research Disclosure*, No. 36544, page 527, *Research Disclosure*, No. 307105, page 872, and *Research Disclosure*, No. 15162, and compounds falling within the formula of representative compounds and compound examples described on pages 127 to 137 of JP-A-62-215272 can be used.

Examples of the antiseptic include sodium dehydroacetate, sodium benzoate, sodium pyridinethione-1-oxide, ethyl p-hydroxybenzoate, and 1,2-benzisothiazolin-3-one and salts thereof. It is preferable that the antiseptic is used in an amount of from 0.02 to 1.00% by weight in the ink.

As the pH adjustor, the foregoing neutralizing agents (organic bases and inorganic alkalis) can be used. For the purpose of improving the storage stability of the inkjet recording ink, it is preferable that the pH adjustor is added such that the inkjet recording ink has a pH of from 6 to 10, and more preferably from 7 to 10 for the summer season.

As the surface tension adjustor, nonionic, cationic or anionic surfactants are enumerated. Incidentally, the surface tension of the inkjet ink of the invention is preferably from 25 to 70 mN/m, and more preferably from 25 to 60 mN/m. Also, it is preferable to adjust the inkjet ink of the invention so as to have a viscosity of not more than 30 mPa·s, and more preferably not more than 20 mPa·s. As the surfactant, anionic surfactants such as fatty acid salts, alkylsulfuric acid ester salts, alkylbenzenesulfonic acid salts, alkylnaphthalenesulfonic acid salts, dialkylsulfosuccinic acid salts, alkylphosphoric acid ester salts, a naphthalenesulfonic acid-formalin condensate, and polyoxyethylene alkylsulfuric acid ester salts; and nonionic surfactants such as polyoxyethylene alkyl ethers, polyoxyethylene alkyl allyl ethers, polyoxyethylene fatty acid esters, sorbitan fatty acid esters, polyoxyethylene sorbitan fatty acid esters, polyoxyethylene alkylamines, glycerin fatty acid esters, and an oxyethylene-oxypropylene block copolymer are preferable. Also, SURFYNOLS (manufactured by Air Products & Chemicals) as an acetylene based polyoxyethylene oxide surfactant can be preferably used. Also, ampholytic surfactants of an amine oxide type, such as N,N-dimethyl-N-alkylamine oxides, are preferable. Further, surfactants described in JP-A-59-157636, pages 37 to 38 and *Research Disclosure*, No. 308119 (1989) can be used.

As the antifoaming agent, fluorine based compounds, silicone based compounds, and chelating agents represented by EDTA can be used, if desired.

In the case where the phthalocyanine compound of the invention is dispersed in an aqueous medium, it is preferable that colored fine particles containing a pigment and an oil-soluble polymer are dispersed in an aqueous medium as described in JP-A-11-286637 and Japanese Patent Application Nos. 2000-78491, 2000-80259 and 2000-62370, or the compound of the invention dissolved in a high-boiling organic solvent is dispersed in an aqueous medium as described in Japanese Patent Application Nos. 2000-78454, 2000-78491, 2000-203856 and 2000-203857. With respect to a specific method in the case of dispersing the compound of the invention in an aqueous medium, as the oil-soluble polymer or high-boiling organic solvent and additives to be used and amounts thereof, those described in the foregoing patent documents can be preferably employed. Alternatively, the phthalocyanine compound may be dispersed in the state of fine particles as it stands as a solid. At the time of dispersion, a dispersant and a surfactant can be used. As a dispersion device, a simple stirrer or impeller agitation mode, an inline agitation mode, a mill mode (such as a colloid mill, a ball mill, a sand mill, an attritor, a roll mill, and an agitator mill), a ultrasonic wave mode, and a high-pressure emulsion dispersion mode (a high-pressure homogenizer; specific examples of commercially available devices include a Gaulin homogenizer, a microfluidizer, and DeBEE 2000) can be employed. With respect to the preparation process of the inkjet recording ink, the details are described in not only the foregoing patent documents but also JP-A-5-148436, JP-A-5-295312, JP-A-7-97541, JP-A-7-82515, JP-A-7-118584, JP-A-11-286637, and Japanese Patent Application No. 2000-87539, and it can be applied to the preparation of the inkjet recording ink of the invention.

The aqueous medium contains water as the main ingredient, and if desired, a mixture in which a water-miscible organic solvent is added can be used. Examples of the water-miscible organic solvent include alcohols (such as methanol, ethanol, propanol, isopropanol, butanol, isobutanol, sec-butanol, t-butanol, pentanol, hexanol, cyclohexanol, and benzyl alcohol); polyhydric alcohols (such as ethylene glycol, diethylene glycol, triethylene glycol, polyethylene glycol, propylene glycol, dipropylene glycol, polypropylene glycol, butylene glycol, hexanediol, pentanediol, glycerin, hexanetriol, and thiodiglycol); glycol derivatives (such as ethylene glycol monomethyl ether, ethylene glycol monoethyl ether, ethylene glycol monobutyl ether, diethylene glycol monomethyl ether, diethylene glycol monobutyl ether, propylene glycol monomethyl ether, propylene glycol monobutyl ether, dipropylene glycol monomethyl ether, triethylene glycol monomethyl ether, ethylene glycol diacetate, ethylene glycol monomethyl ether acetate, triethylene glycol monomethyl ether, triethylene glycol monoethyl ether, and ethylene glycol monophenyl ether);

amines (such as ethanolamine, diethanolamine, triethanolamine, N-methyldiethanolamine, N-ethyldiethanolamine, morpholine, N-ethylmorpholine, ethylenediamine, diethylenetriamine, triethylenetetramine, polyethyleneimine, and tetramethylpropylenediamine); and other polar solvents (such as formamide, N,N-dimethylformamide, N,N-dimethylacetamide, dimethyl sulfoxide, sulfolane, 2-pyrrolidone, N-methyl-2-pyrrolidone, N-vinyl-2-pyrrolidone, 2-oxazolidone, 1,3-dimethyl-2-imidazolidinone, acetonitrile, and acetone). Incidentally, the water-miscible organic solvent may be used in admixture of two or more thereof.

It is preferable that the phthalocyanine compound is contained in an amount of from 0.2 parts by weight to 10 parts by weight in 100 parts by weight of the inkjet recording ink of the invention. Also, other pigment may be used in combination with the phthalocyanine compound in the inkjet ink of the invention. In the case where two or more kinds of pigments are used in combination, it is preferable that the total content of the pigments falls within the foregoing range.

It is preferable that the inkjet recording ink of the invention has a viscosity of not more than 30 mPa·s. Also, it is preferable that the inkjet recording ink of the invention has a surface tension of from 25 mN/m to 70 mN/m. The viscosity and surface tension can be adjusted by the addition of various additives such as a viscosity adjustor, a surface tension adjustor, a specific resistance adjustor, a film adjustor, a ultraviolet absorber, an antioxidant, a color fading preventive, an antiseptic, a rust preventive, a dispersant, and a surfactant.

The inkjet recording ink of the invention can be used for not only monochromatic image formation but also full-color image formation. For the sake of forming a full-color image, a magenta color ink, a cyan color ink, and a yellow color ink can be used. Also, for the sake of adjusting the color tone, a black color ink may further be used.

As yellow dyes that can be applied, arbitrary yellow dyes can be used. Examples include aryl or heteryl azo dyes containing, for example, phenols, naphthols, anilines, heterocyclic compounds (such as pyrazolone and pyridone), or open chain type active methylene compounds as a coupling component (hereinafter referred to as "coupler component"); azo methine dyes containing, for example, open chain type active methylene compounds as the coupling component; methine dyes such as benzylidene dyes and monomethine oxonol dyes; quinone dyes such as naphthoquinone dyes and anthraquinone dyes; and other dyes such as quinophthalone dyes, nitro-nitroso dyes, acridine dyes, and acridinone dyes.

As magenta dyes that can be applied, arbitrary magenta dyes can be used. Examples include aryl or heteryl azo dyes containing, for example, phenols, naphthols, or anilines as the coupler component; azo methine dyes containing, for example, pyrazolones or pyrazolotriazoles as the coupler component; methine dyes such as arylidene dyes, styryl dyes, merocyanine dyes, cyanine dyes, and oxonol dyes; carbonium dyes such as diphenylmethane dyes, triphenylmethane dyes, and xantbene dyes; quinone dyes such as naphthoquinone, anthraquinone, and anthrapyridone; and fused polycyclic dyes such as dioxazine dyes.

As cyan dyes that can be applied, arbitrary cyane dyes can be used. Examples include aryl or heteryl azo dyes containing, for example, phenols, naphthols, or anilines as the coupler component; azo methine dyes containing, for example, phenols, naphthols, or pyrrolotriazoles as the coupler component; polymethine dyes such as cyanine dyes, oxonol dyes, and merocyanine dyes; carbonium dyes such as diphenylmethane dyes, triphenylmethane dyes, and xanthene dyes; phthalocyanine dyes; anthraquinone dyes; and indigo-thioindigo dyes.

The foregoing dyes may be ones that exhibit yellow, magenta and cyan colors, respectively first when a part of the chromophore is dissociated. In that case, the counter cation may be an inorganic cation such as an alkali metal and ammonium or an organic cation such a pyridinium or quaternary ammonium salt, or may be a polymer cation containing the same as a partial structure.

As black coloring materials that can be applied, dispersions of carbon black can be enumerated in addition to disazo, trisazo and tetraazo dyes.

[Inkjet Recording Method]

The inkjet recording method of the invention comprises providing the inkjet recording ink with energy to form an image on a known image receiving material, i.e., plain paper or resin-coated paper, such as inkjet dedicated papers, films, electrophotographic shared papers, fabrics, glass, metals, and potteries as described in JP-A-8-169172, JP-A-8-27693, JP-A-2-276670, JP-A-7-276789, JP-A-9-323475, JP-A-62-238783, JP-A-10-153989, JP-A-10-217473, JP-A-10-235995, JP-A-10-337947, JP-A-10-217597, and JP-A-10-337947.

In forming an image, a polymer fine particle dispersion (sometimes called "polymer latex") may be jointly used for the purposes of imparting gloss or resistance to water and improving weather resistance. The timing of providing the image receiving material with a polymer latex may be prior to or after or at the same time of adding a coloring agent. Accordingly, the polymer latex may be added in the image receiving paper or in the ink, or the polymer latex may be used singly as a liquid material. Concretely, methods described in Japanese Patent Application Nos. 2000-363090, 2000-315231, 2000-354380, 2000-343944, 2000-268952, 2000-299465, and 2000-297365 can be preferably employed.

Recording papers or recording films to be used for carrying out inkjet printing using the ink of the invention will be described below.

As a support in the recording paper or recording film, those made of a chemical pulp such as LBKP and NBKP; a mechanical pulp such as GP, PGW, RMP, TMP, CTMP, CMP, and CGP; or a waste paper pulp such as DIP, to which conventionally known additives such as pigments, binders, sizing agents, fixing agents, cationic agents, and paper strength additives are added, if desired, and produced by various devices such as a fourdrinner paper machine and a cylinder paper machine can be employed. Besides these supports, synthetic papers and plastic film sheets may also be employed. The support preferably has a thickness of from 10 to 250 μm and a basis weight of from 10 to 250 g/m².

The support may be provided directly with an ink receiving layer or a backcoat layer, or may be provided with an ink receiving layer or a backcoat layer after size pressing with starch, polyvinyl alcohol, etc. or providing an anchor coat layer. Further, the support may be flattened by a calendering device such as a machine calender, a TG calender, and a soft calender. In the invention, papers or plastic films, the both surfaces of which are laminated with a polyolefin (such as polyethylene, polystyrene, polyethylene terephthalate, polybutene, and copolymers thereof), are more preferably used as the support.

It is preferable that a white pigment (such as titanium white and zinc oxide) or a toning dye (such as cobalt blue, ultramarine, and neodymium oxide) is added in the polyolefin.

In the ink receiving layer to be provided on the support, a pigment and an aqueous binder are contained. As the pigment, white pigments are preferable, examples of which include white inorganic pigments such as calcium carbonate, kaolin, talc, clay, diatomaceous earth, synthetic amorphous silica, aluminum silicate, magnesium silicate, calcium silicate, aluminum hydroxide, alumina, lithopone, zeolite, barium sulfate, calcium sulfate, titanium dioxide, zinc sulfide, and zinc carbonate; and organic pigments such as styrene based pigments, acrylic pigments, urea resins, and melamine resins. As the white pigment to be contained in the ink receiving layer, porous inorganic pigments are preferable, and synthetic amorphous silica having a large pore area is especially suitable. With respect to the synthetic amorphous silica, any of anhydrous silicate obtained by the dry production process and hydrated silicate obtained by the wet production process can be employed, and the use of hydrated silicate is especially desired.

Examples of the aqueous binder to be contained in the ink receiving layer include water-soluble high-molecular compounds such as polyvinyl alcohol, silanol-modified polyvinyl alcohol, starch, cationic starch, casein, gelatin, carboxymethyl cellulose, hydroxyethyl cellulose, polyvinylpyrrolidone, polyalkylene oxides, and polyalkylene oxide derivatives; and water-dispersible high-molecular compounds such as a styrene-butadiene latex and acrylic emulsions. The aqueous binder can be used singly or in admixture of two or more thereof. In the invention, above all, polyvinyl alcohol and silanol-modified polyvinyl alcohol are especially suitable from the standpoints of adhesion and resistance to peeling of the ink receiving layer.

The ink receiving layer can contain a mordant, a waterproofing agent, a light resistance improver, a surfactant, and other additives in addition to the pigment and aqueous binder.

It is preferable that the mordant to be added in the ink receiving layer is immobilized. For achieving this purpose, a polymer mordant is preferably used.

The polymer mordant is described in JP-A-48-28325, JP-A-54-74430, JP-A-54-124726, JP-A-55-22766, JP-A-55-142339, JP-A-60-23850, JP-A-60-23851, JP-A-60-23852, JP-A-60-23853, JP-A-60-57836, JP-A-60-60643, JP-A-60-118834, JP-A-60-122940, JP-A-60-122941, JP-A-60-122942, JP-A-60-235134, JP-A-1-161236, and U.S. Pat. Nos. 2,484,430, 2,548,564, 3,148,061, 3,309,690, 4,115,124, 4,124,386, 4,193,800, 4,273,853, 4,282,305, and 4,450,224. Image receiving materials containing a polymer mordant described on pages 212 to 215 of JP-A-1-161236 are especially preferable. When the polymer mordant described in the subject patent document is used, images having excellent image quality are obtained, and the resistance to light of an image is improved.

The waterproofing agent is effective for waterproofing the image, and as the waterproofing agent, cationic resins are desired. Examples of cationic resins include polyamidepolyamine epichlorohydrin, polyethyleneimine, polyaminesulfone, dimethyldiallyammonium chloride polymers, cationic polyacrylamide, and colloidal silica. Of these cationic resins, polyamidepolyamine epichlorohydrin is especially suitable. The content of the cationic resin is preferably from 1 to 15% by weight, and especially preferably from 3 to 10% by weight based on the whole of solids of the ink receiving layer.

Examples of the light resistance improver include zinc sulfate, zinc oxide, hindered amine based antioxidants, and benzotriazole based ultraviolet absorbers such as benzophenone. Of these, zinc sulfate is especially suitable.

The surfactant functions as a coating aid, a release improver, a slipperiness improver, or an antistatic. The surfactant is described in JP-A-62-173463 and JP-A-62-183457. An organic fluoro compound may be used in place of the surfactant. It is preferable that the organic fluoro compound is hydrophobic. Examples of the organic fluoro compound include fluorine based surfactants, oily fluorine based compounds (for example, fluoro oils), and solid-state fluoro compound resins (for example, tetrafluoroethylene resins). The organic fluoro compounds are described in JP-B-57-9053 (columns 8 to 17), JP-A-61-20994, and JP-A-62-135826. As other additives to be added in the ink receiving layer, pigment dispersants, thickeners, antifoaming agents, dyes, fluorescent brighteners, antiseptics, pH adjustors, matting agents, and hardeners are enumerated. Incidentally, the ink receiving layer may be of a mono-layer or double-layer structure.

The recording paper or recording film may be provided with a backcoat layer. As components that can be added in the backcoat layer, white pigments, aqueous binders, and other components are enumerated. Examples of white pigments that are contained in the backcoat layer include white inorganic pigments such as precipitated calcium carbonate light, calcium carbonate heavy, kaolin, talc, calcium sulfate, barium sulfate, titanium dioxide, zinc oxide, zinc sulfide, zinc carbonate, satin white, aluminum silicate, diatomaceous earth, calcium silicate, magnesium silicate, synthetic amorphous silica, colloidal silica, colloidal alumina, pseudoboehmite, aluminum hydroxide, alumina, lithopone, zeclite, hydrated halloysite, magnesium carbonate, and magnesium hydroxide; and organic pigments such as styrene based plastic pigments, acrylic plastic pigments, polyethylene, microcapsules, urea resins, and melamine resins.

Examples of aqueous binders that are contained in the backcoat layer include water-soluble high-molecular compounds such as styrene/maleic acid salt copolymers, styrene/acrylic acid salts copolymers, polyvinyl alcohol, silanol-modified polyvinyl alcohol, starch, cationic starch, casein, gelatin, carboxymethyl cellulose, hydroxyethyl cellulose, and polyvinylpyrrolidone; and water-dispersible high-molecular compounds such as a styrene-butadiene latex and acrylic emulsions. As other components that are contained in the backcoat layer, an antifoaming agent, a foam inhibitor, a dye, a fluorescent brightener, an antiseptic, and a waterproofing agent are enumerated.

In the constitutional layers (including the backcoat layer) of the inkjet recording paper or recording film, a polymer latex may be added. The polymer latex is used for the purpose of improving film physical properties such as dimensional stabilization, curl prevention, adhesion prevention, and crazing prevention of film. The polymer latex is described in JP-A-62-245258, JP-A-62-136648, and JP-A-62-110066. When a polymer latex having a low glass transition temperature (not higher than 40° C.) is added to a layer containing a mordant, it is possible to prevent crazing or curl of the layer. Also, even when a polymer latex having a high glass transition temperature is added to the backcoat layer, it is possible to prevent curl of the layer.

The ink of the invention is not limited with respect to the inkjet recording mode, but known modes can be employed. Examples include a charge control mode of ejecting an ink utilizing an electrostatic induction force, a drop on-demand mode utilizing a vibration pressure of piezoelectric device (pressure pulse mode), an acoustic inkjet mode of converting electric signals to acoustic beams, irradiating an ink with the beams and ejecting the ink utilizing a radiation pressure, and a thermal inkjet mode of heating an ink to form bubbles and utilizing a generated pressure. The inkjet recording mode includes a mode of injecting a number of small areas of an ink having a low concentration called a photo ink, a mode of improving the image quality using plural inks having substantially the same hue and a different concentration, and a mode of using a colorless transparent ink.

EXAMPLES

Synthesis Examples

The synthesis of the phthalocyanine compound (or mixture) of the invention will be described below in detail with reference to the following Examples, but it should not be construed that the invention is limited thereto.

Representative phthalocyanine compounds (or mixtures) of the invention can be derived from, for example, the following synthesis route. In the following Examples, λmax means an absorption maximum wavelength; and εmax means a molar absorptivity at the absorption maximum wavelength.

Values of oxidation potential of substituted phthalocyanine compounds of the invention as synthesized in the following Examples (Synthesis Examples) and Comparative Compounds 1 to 3 were measured under the following conditions. That is, the oxidation potential was measured in N,N-dimethylformamide containing 0.1 moles/dm$^3$ of tetrapropylammonium perchlorate as a supporting electrolyte (concentration of the compound: 0.001 moles/dm$^3$) using graphite electrodes and using POLAR GRAPHIC ANLYZER P-1100 (produced by YANACO) by means of direct current polarography. The values of oxidation potential (vs SCE) of the substituted phthalocyanine compounds as measured are shown in Table 6 below.

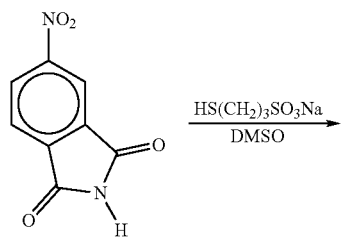

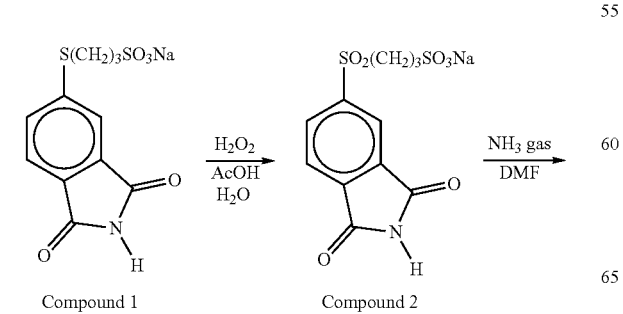

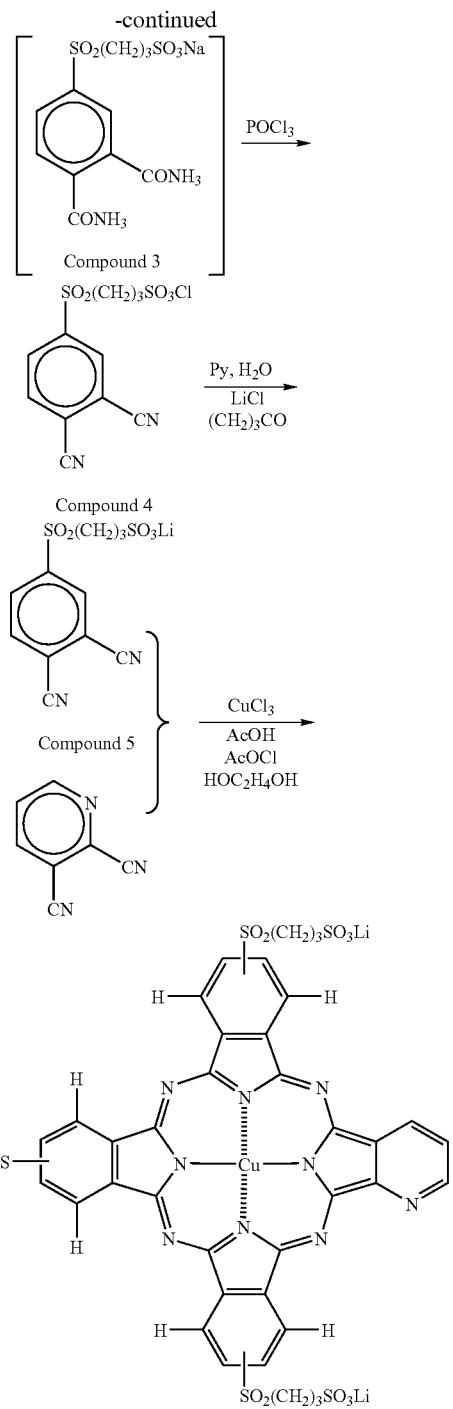

Synthesis Example 1

Synthesis of Compound 1

Under a nitrogen gas stream, 288.2 g of 4-nitrophthalimide (manufactured by Tokyo Kasei Kogyo Co., Ltd.) was dissolved in 1,442 mL of DMSO (dimethyl sulfoxide), to which was then added 333 g of sodium 3-mercpto-propanesulfonate (85%) while stirring at an internal temperature of 20° C. Subsequently, 173.8 g of anhydrous sodium carbonate was gradually added to the mixture while stirring at an internal temperature of 50° C. The reaction mixture was heated to 70° C. while stirring, and stirring was continued at the same temperature for one hour. After cooling to 40° C., the reaction mixture was filtered by a nutsche filter, and the filtrate was poured into 2,885 mL of methanol and crystallized. Subsequently, the mixture was stirred at room temperature for 30 minutes, into which was then poured 1,442 mL of isopropanol, and the mixture was cooled to an internal temperature of 10° C. while stirring. Deposited crude crystals were filtered by a nutsche filter and washed with 962 mL of methanol, followed by drying to obtain 503.4 g of crude crystals of Compound 1. $^1$H-NMR (DMSO-d6), δ values (TMS as a standard): 1.89 to 1.99 (2H, m); 2.51 to 2.65 (2H, t); 3.24 to 3.50 (2H, t); 7.64 to 7.76 (3H, m); 11.29 to 11.41 (1H, s).

Synthesis Example 2

Synthesis of Compound 2

Compound 1 (485.0 g) was added to a mixed solution of 48.5 mL of acetic acid and 1,500 mL of $H_2O$, and 15 g of $Na_2WO_4.2H_2O$ was added to the mixture while stirring at an internal temperature of 25° C. The temperature was then raised to an internal temperature of 45° C., thereby dissolving the mixture. Subsequently, 374 mL of aqueous hydrogen peroxide (30%) was gradually added dropwise while taking care of heat generation. After stirring at an internal temperature of 50° C. for 60 minutes, 88.2 g/400 mL of an aqueous solution of sodium sulfite was added dropwise to the reaction mixture at an internal temperature of 50° C., to which was then added dropwise 532 mL of isopropanol at the same temperature, followed by cooling to 10° C. Subsequently, stirring was continued at the same temperature for 30 minutes, and deposited crystals were filtered by a nutsche filter and washed with 525 mL of isopropanol, followed by drying to obtain 462.6 g of Compound 2. $^1$H-NMR (DMSO-d6), δ values (TMS as a standard): 1.25 to 1.89 (2H, m); 2.48 to 2.52 (2H, t); 3.59 to 3.65 (2H, t); 8.04 to 8.11 (1H, d); 8.20 (1H, s); 8.29 to 8.33 (1H, d); 11.59 to 11.90 (1H, s).

Synthesis Example 3

Synthesis of Compound 3

Compound 2 (300 g) was added to 900 mL of DMF (dimethylformamide), an $NH_3$ gas was brown into the mixture for 90 minutes while stirring at an internal temperature of 20° C., and stirring was continued at the same temperature for 3 hours. Next, the reaction mixture was stirred in vacuo (<400 mmHg) at an internal temperature of not higher than 20° C., thereby distilling off the dissolved residual $NH_3$ gas (Compound 2+$NH_3$→reaction mixture of Compound 3).

Synthesis Example 4

Synthesis of Compound 4

To 600 mL of DMF (dimethylformamide) at an internal temperature of 5° C., 315.1 mL of $POCl_3$ was added dropwise while keeping an internal temperature at not higher than 15° C. Subsequently, the reaction mixture of the foregoing Synthesis Example 3 (Compound 2+$NH_3$→Compound 3) was added dropwise to the $POCl_3$/DMF solution while keeping an internal temperature at not higher than 10° C., and the mixture was subsequently stirred at an internal temperature of 17° C. for one hour. Next, the reaction mixture was added dropwise to 4,500 mL of $H_2O$ while keeping an internal temperature at not higher than 35° C. to crystallize Compound 4. Subsequently, the reaction mixture was stirred at an internal temperature of 30° C. for 30 minutes, and the deposited crude crystals were filtered by a nutsche filter, washed with 4,200 mL of $H_2O$, washed with 2,700 mL of isopropanol, and then air dried to obtain 234.6 g of Compound 4. $^1$H-NMR (DMSO-d6), δ values (TMS as a standard): 1.81 to 1.91 (2H, m); 2.49 to 2.54 (2H, t); 3.62 to 3.74 (2H, t); 8.07 to 8.16 (1H, d); 8.36 to 8.49 (1H, d); 8.66 to 8.67 (2H, s).

Synthesis Example 5

Synthesis of Compound 5

Compound 4 (100 g) was dissolved in 400 mL of acetone at an internal temperature of 35° C., into which was then poured 45 mL of $H_2O$, and the mixture was cooled to an internal temperature of 20° C. while stirring. Next, 49 mL of pyridine was added dropwise at a rate such that an internal temperature did not exceed 40° C., and the internal temperature was subsequently raised to 55° C., followed by stirring at the same temperature for 2 hours. Next, a solution of 34 g of lithium chloride in 750 mL of isopropanol was added dropwise at the same temperature, and stirring was subsequently continued at the same temperature for one hour, followed by cooling to room temperature step-by-step. Deposited crystals were filtered by a nutsche filter, washed with 1,000 mL of isopropanol, and dried to obtain 86.5 g of Compound 5. $^1$H-NMR (DMSO-d6), δ values (TMS as a standard): 1.81 to 1.91 (2H, m); 2.29 to 2.54 (2H, t); 3.62 to 3.67 (2H, t); 8.07 to 8.16 (1H, d); 8.30 to 8.36 (1H, d); 8.66 (1H, s).

Example 1

Synthesis of Compound 101

Compound 5 (19.22 g) and 2.58 g of pyridine-2,3-dicarbonitrile (manufactured by Tokyo Kasei Kogyo Co., Ltd.) were dissolved in a mixed solution of 2.28 mL of acetic acid and 135.22 mL of diethylene glycol at an internal temperature of 102° C. Subsequently, the internal temperature was cooled to 84° C., and 5.16 g of lithium acetate and 2.69 g of cupric chloride (anhydrous) were added, followed by raising the internal temperature to 90° C. Stirring was continued at the same temperature for 4 hours, and after raising the internal temperature to 91° C., 59.42 mL of concentrated hydrochloric acid was added dropwise. Subsequently, stirring was continued at the same temperature for 30 minutes, and after cooling the internal temperature to 70° C., 3.84 g of lithium chloride was added, to which was then added dropwise 540 mL of isopropanol at the same temperature, thereby causing crystallization. Next, after cooling the internal temperature to 23° C., the deposited crystals were filtered and washed with 1,000 mL of isopropanol. The crude crystals (16.0 g) after drying were dissolved in a mixed solution of 20 mL of methanol and 60 mL of ion-exchanged water, and an aqueous solution of 2.5N LiOH was added at 50° C. until the pH became 9.7. Subsequently, the resulting aqueous solution was filtered at the same temperature to eliminate the contaminants. After raising an internal temperature of the filtrate to 90° C., stirring was continued at the same temperature for 30 minutes, and 240 mL of isopropanol was added dropwise, thereby causing crystallization. After cooling a suspension to room temperature, the deposited crystals were subjected to suction filtration, washed with 960 mL of isopropanol, and dried at 80° C. for 30 hours. Yield: 13.45 g. Solution absorption: λmax=626 nm, ε=52,300 ($H_2O$).

Example 2

Synthesis of Compound 102

Compound 5 (19.22 g) and 2.58 g of 3,4-pyridine-dicarbonitrile (manufactured by Aldrich) were dissolved in a mixed solution of 2.28 mL of acetic acid and 135.22 mL of diethylene glycol at an internal temperature of 105° C. Subsequently, the internal temperature was cooled to 84° C., and 5.16 g of lithium acetate and 2.69 g of cupric chloride (anhydrous) were added, followed by raising the internal temperature to 90° C. Stirring was continued at the same temperature for 4 hours, and after raising the internal temperature to 91° C., 59.42 mL of concentrated hydrochloric acid was added dropwise. Subsequently, stirring was continued at the same temperature for 30 minutes, and after cooling the internal temperature to 70° C., 3.84 g of lithium chloride was added, to which was then added dropwise 541 mL of isopropanol at the same temperature, thereby causing crystallization. Next, after cooling the internal temperature to 23° C., the deposited crystals were filtered and washed with 1,082 mL of isopropanol. The crude crystals (18.0 g) after drying were dissolved in a mixed solution of 22.5 mL of methanol and 67.5 mL of ion-exchanged water, and an aqueous solution of 2.5N LiOH was added at 50° C. until the pH became 9.7. Subsequently, the resulting aqueous solution was filtered at the same temperature to eliminate the contaminants. After raising an internal temperature of the filtrate to 90° C., stirring was continued at the same temperature for 30 minutes, and 270 mL of isopropanol was added dropwise, thereby causing crystallization. After cooling a suspension to room temperature, the deposited crystals were subjected to suction filtration, washed with 1,080 mL of isopropanol, and dried at 80° C. for 30 hours. Yield: 14.91 g. Solution absorption: λmax=625 nm, ε=56,336 ($H_2O$).

Example 3

Synthesis of Compound 103

Compound 5 (19.22 g) and 2.60 g of 2,3-pyrazine-dicarbonitrile (manufactured by Aldrich) were dissolved in a mixed solution of 2.28 mL of acetic acid and 135.22 mL of diethylene glycol at an internal temperature of 110° C. Subsequently, the internal temperature was cooled to 83° C., and 5.16 g of lithium acetate and 2.69 g of cupric chloride (anhydrous) were added, followed by raising the internal temperature to 90° C. Stirring was continued at the same temperature for 4 hours, and after raising the internal temperature to 91° C., 59.42 mL of concentrated hydrochloric acid was added dropwise. Subsequently, stirring was continued at the same temperature for 30 minutes, and after cooling the internal temperature to 70° C., 3.84 g of lithium chloride was added, to which was then added dropwise 541 mL of isopropanol at the same temperature, thereby causing crystallization. Next, after cooling the internal temperature to 23° C., the deposited crystals were filtered and washed with 1,082 mL of isopropanol. The crude crystals (14.0 g) after drying were dissolved in a mixed solution of 17.5 mL of methanol and 52.5 mL of ion-exchanged water, and an aqueous solution of 2.5N LiOH was added at 50° C. until the pH became 9.7. Subsequently, the resulting aqueous solution was filtered at the same temperature to eliminate the contaminants. After raising an internal temperature of the filtrate to 90° C., stirring was continued at the same temperature for 30 minutes, and 210 mL of isopropanol was added dropwise, thereby causing crystallization. After cooling a suspension to room temperature, the deposited crystals were subjected to suction filtration, washed with 840 mL of isopropanol, and dried at 80° C. for 30 hours. Yield: 13.54 g. Solution absorption: λmax=623 nm, ε=52,000 ($H_2O$).

Synthesis of Comparative Compounds

Synthesis of Comparative Compound 1

In a three-necked flask equipped with a condenser, 150 mL of chlorosulfonic acid was charged, to which was then dividedly added 25.0 g of copper phthalocyanine step-by-step with stirring while keeping the temperature such that it did not exceed 20° C. (cooling was carried out simultaneously because heat generation occurred). Subsequently, this mixture was heated to 100° C. over one hour and further heated to 135° C. over one hour, and stirring was continued at the same temperature for 5 hours until the generation of gases was completed. Thereafter, the reaction mixture was cooled to 10° C. and then gradually added to a mixture of 1,500 mL of saturated salt water and 500 g of ice to deposit a desired product as a blue crystal. The temperature in the suspension was kept at from 0 to 5° C. by complementarily adding ice. Further, the mixture was stirred at room temperature for one hour, filtered by a nutsche filer, and washed with a 1,000 mL of cold saturated salt water. The resulting solids were dissolved in 700 mL of a 0.1 M sodium hydroxide aqueous solution. The solution was heated to 80° C. while stirring, and stirring was continued at the same temperature for one hour. The aqueous solution was filtered at heating to eliminate the contaminants, and 270 mL of sodium chloride was gradually added to the filtrate while stirring, thereby causing salting out. The resulting solution was heated to 80° C. while stirring, and stirring was continued at the same temperature for one hour. After cooling to room temperature, deposited crystals were filtered and washed with 150 mL of 20% salt water. Subsequently, the resulting crystals were added to 200 mL of 80% ethanol and stirred under reflux conditions for one hour. After cooling to room temperature, deposited crystals were filtered, and the resulting crystals were added to 200 mL of a 60% ethanol aqueous solution and stirred under reflux conditions for one hour. After cooling to room temperature, deposited crystals were filtered, washed with 300 mL of ethanol, and dried to obtain 34.2 g of the following Comparative Compound 1 as a blue crystal. λmax: 624.8 nm; εmax=$3.40 \times 10^4$; λmax: 663.8 nm; εmax=$3.57 \times 10^4$ (in aqueous solution). As a result of analysis of the resulting compound, it could be confirmed that the compound was a mixture having a substitution ratio of sulfo group of about 4:3:2=1:3:1 (ESI-MS).

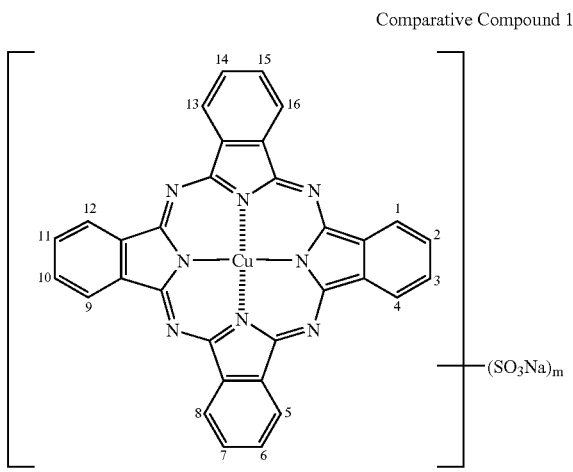

Comparative Compound 1

Substitution positon: mixture of 1-position to 16-position
Substitution number: mixture of m = 4, 3, 2

Synthesis of Comparative Compound 2:

In a three-necked flask equipped with a condenser, 100 mL of nitrobenzene was charged. After raising the temperature to 180° C. over one hour, 43.2 g of sodium 4-sulfophthalate, 4.7 g of ammonium chloride, 58 g of urea, 0.68 g of ammonium molybdate, and 6.93 g of copper(II) chloride were added, and stirring was continued at the same temperature for 6 hours. After cooling the reaction mixture to 40° C., 200 mL of methanol heated at 50° C. was poured, and stirring was continued at room temperature for one hour while pulverizing formed solids. The resulting dispersion was filtered by a nutsche filter and washed with 400 mL of methanol. Subsequently, the resulting solids were added to 1,000 mL of a 1M hydrochloric acid aqueous solution saturated with sodium chloride, and the mixture was boiled to elute the unreacted copper salt. After cooling, the precipitated solids were filtered by a nutsche filter and washed with 100 mL of a 1M hydrochloric acid saturated salt aqueous solution. The resulting solids were dissolved in 700 mL of a 0.1 M sodium hydroxide aqueous solution. The solution was heated to 80° C. while stirring, and stirring was continued at the same temperature for one hour. The aqueous solution was filtered at heating to eliminate the contaminants, and 270 mL of sodium chloride was gradually added to the filtrate while stirring, thereby causing salting out. The resulting solution was heated to 80° C. while stirring, and stirring was continued at the same temperature for one hour. After cooling to room temperature, deposited crystals were filtered and washed with 150 mL of 20% salt water. Subsequently, the resulting crystals were added to 200 mL of 80% ethanol and stirred under reflux conditions for one hour. After cooling to room temperature, deposited crystals were filtered, and the resulting crystals were added to 200 mL of a 60% ethanol aqueous solution and stirred under reflux conditions for one hour. After cooling to room temperature, deposited crystals were filtered, washed with 300 mL of ethanol, and dried to obtain 29.25 g of the following Comparative Compound 2 as a blue crystal. λmax: 629.9 nm; εmax=6.11×10⁴ (in aqueous solution). As a result of analysis of the resulting compound (mass analysis: measured by various instrumental analysis methods such as ESI-MS, elemental analysis, and neutralization titration), it could be confirmed that the compound had the following structure having four sulfo groups in total in one copper phthalocyanine molecule.

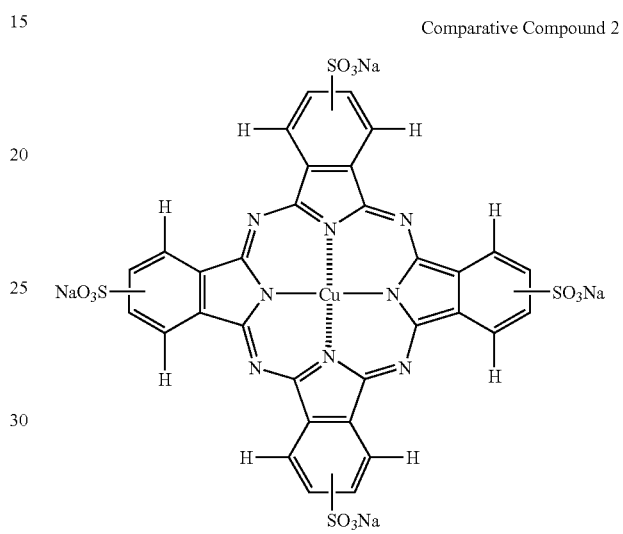

Comparative Compound 2

Example 4

Deionized water was added to the following components to make one liter, and the mixture was stirred for one minute while heating at from 30 to 40° C. Thereafter, the reaction mixture was adjusted at a pH of 9 with 10 moles/L of KOH and filtered in vacuo by a microfilter having a mean pore diameter of 0.25 μm to prepare a cyan ink solution.

| Formulation of Ink Solution A: | |
|---|---|
| Phthalocyanine dye mixture of the invention (Illustrative Compound 101): | 6.80 g |
| Diethylene glycol: | 10.65 g |
| Glycerin: | 14.70 g |
| Diethylene glycol monobutyl ether: | 12.70 g |
| Triethanolamine: | 0.65 g |
| Olefin E1010: | 0.9 g |

Ink Solutions B to E were prepared in the same manner as in the preparation of the Ink Solution A, except for changing the phthalocyanine dye composition as in the following Table 6, and Ink Solutions 101, 102 and 103 were prepared using the following compounds, respectively.

TABLE 6

| Sample No. | Pigment No. | Color tone | Paper dependency | Resistance to water | Resistance to light | Dark heat preservability | Resistance to ozone gas | Ink storage stability | Solubility | Recovery of clogging | Oxidation potential (Eox) |
|---|---|---|---|---|---|---|---|---|---|---|---|
| Ink Solution A | 101 | A | A | A | A | A | A | A | A | A | A |
| Ink Solution B | 102 | A | A | A | A | A | A | A | A | A | A |
| Ink Solution C | 103 | A | A | A | A | A | A | A | A | A | A |
| Ink Solution D | 105 | A | A | A | A | A | A | A | A | A | A |
| Ink Solution E | 106 | A | A | A | A | A | A | A | A | A | A |
| Ink Solution 101 | Comparative Compound 1 | B | B | B | C | B | C | A | A | A | B (0.75) |
| Ink Solution 102 | Comparative Compound 2 | B | B | B | A | B | C | B | B | B | B (0.91) |
| Ink Solution 103 | Comparative Compound 3 | B | A | B | A | B | C | C | C | C | B (0.85) |

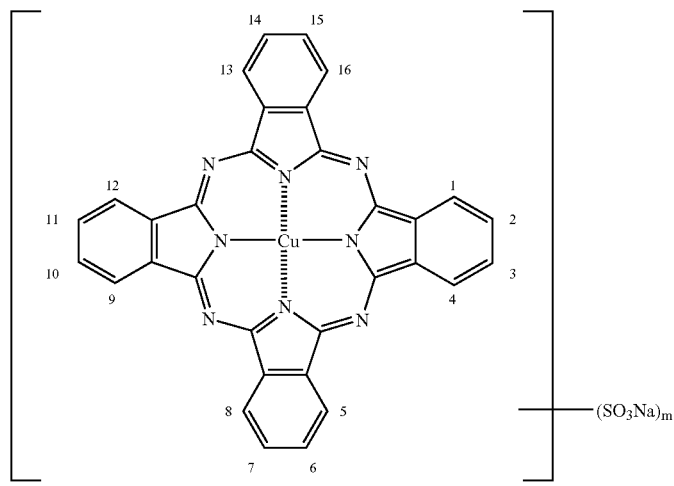

Substitution position: mixture of 1-position to 16-position

Substitution number: mixture of m = 4, 3, 2

Comparative Compound 1

TABLE 6-continued

| Sample No. | Pigment No. | Color tone | Paper depen- dency | Resistance to water | Resistance to light | Dark heat preservability | Resistance to ozone gas | Ink storage stability | Solu- bility | Recovery of clogging | Oxidation potential (Eox) |
|---|---|---|---|---|---|---|---|---|---|---|---|

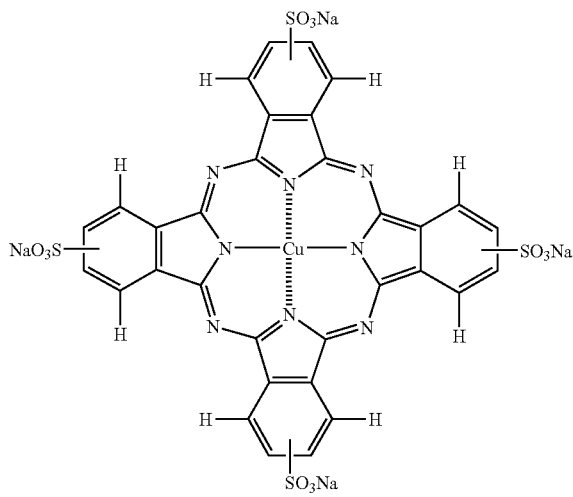

Comparative Compound 2

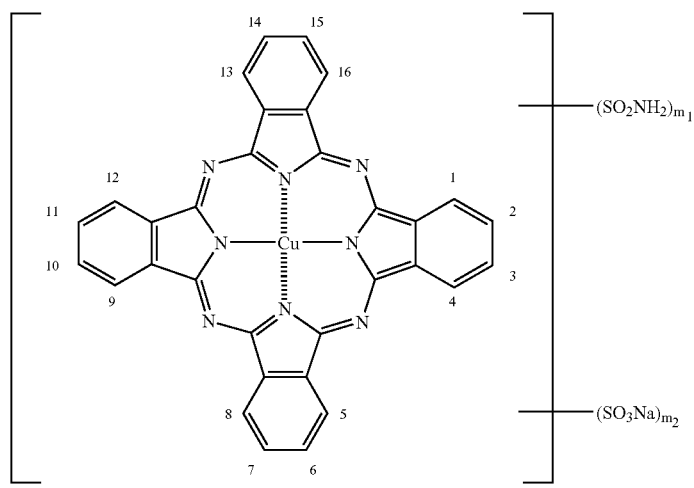

Substitution position: mixture of 1-position to 16-position
Substitution number: mixture of m = 4, 3, 2, m = $m_1 + m_2$
Comparative Compound 3

In the case of changing the dye, the dye was used such that its addition amount was an equimolar amount to the dye used in the Ink Solution A. In the case of two or more kinds of dyes in combination, the dyes were used in equimolar amounts, respectively.

(Image Recording and Evaluation)

With respect to the inkjet inks of the respective Examples (Ink Solutions A to E) and Comparative Examples (Ink Solutions 101 to 103), the following evaluations were carried out. The results obtained are shown in Table 6.

Incidentally, in Table 6, the "color tone", "paper dependency", "resistance to water", and "resistance to light" were each evaluated after recording an image on photo glossy paper (PM photographic paper <Kotaku> (KA420PSK, EPSON) manufactured by Epson Corporation) using an inkjet printer (PM-700C, manufactured by Epson Corporation) using each inkjet ink.

<Color Tone>

With respect to the image formed on the photographic glossy paper, a reflection spectrum at an interval of 10 nm in a region of from 390 to 730 nm was subjected to colorimetry using GRETAG SPM100-II (manufactured by GRETAG), from which were calculated a* and b* based on a CIE (International Commission on Illumination) L*a*b* color space system.

In comparison of a color sample of standard cyan of JAPAN Colour (a color when printing was carried out using Japan Colour Ink SF-90 and Japan Paper such that solid patches of proof prints provided from 21 companies of the members of the Japan Federation of Printing Industries were subjected to colorimetry, and a color difference (ΔE) against an average value thereof became minimum) of JNC (Japan Printing Machinery Manufacturers Association), a preferred color tone as cyan was defined as follows.

L*: Within the range of 53.6±0.2
A: a* (range of −35.9±6) and b* (range of −50.4±6)
B: only one of a* and b* (a preferred region defined with the foregoing "A")
C: any of a* and b* (outside a preferred region defined with the foregoing "A")

The colorimetry values of the color sample of standard cyan of JAPAN Colour as used herein for reference are shown below.

L*: 53.6±0.2
a*: −37.4±0.2
b*: −50.2±0.2
ΔE: 0.4 (from 0.1 to 0.7)

(1) Printing machine: MAN ROLAND R-704, Ink: Japan Colour SF-90, Paper: Tokubishi ART
(2) Colorimetry: Colorimeter; X-Rite 938, 0/45, D50, 2 deg., black backing <Paper Dependency>

The image formed on the photographic glossy paper was compared in color tone with an image separately formed on a professional photo paper PR101 (QBJPRA4, manufactured by CANON) and evaluated according to the following two grades. That is, the case where a difference between the both images was small was designated as A (good), and the case where a difference between the both images was large was designated as B (poor), respectively.

<Resistance to Water>

The photographic glossy paper having an image formed thereon was dried at room temperature for one hour, dipped in deionized water for 10 seconds, and spontaneously dried at room temperature, and bleeding was observed and evaluated according to the following three grades. That is, the case where no bleeding was observed was designated as A, the case where bleeding was slightly observed was designated as B, and the case where bleeding was largely observed was designated as C, respectively.

<Water to Light>

The photographic glossy paper having an image formed thereon was irradiated with xenon light (85,000 1×) for 14 days using a weather-o-meter (Atlas C.I65), and the image density before and after the xenon irradiation was measured using a reflection densitometer (X-Rite 310TR) and evaluated as a retention rate of pigment. Incidentally, the reflection density was measured at three points of 1, 1.5 and 2.0.

The retention rate of pigment was evaluated according to the following three grades. That is, the case where the retention rate of pigment was 70% or more at any of the densities was designated as A, the case where the retention rate of pigment was less than 70% at one or two points was designated as B, and the case where the retention rate of pigment was less than 70% at all of the densities was designated as C, respectively.

<Dark Heat Preservability>

The photographic glossy paper having an image formed thereon was preserved under conditions at 80° C. and at 15% RH for 14 days, and the image density before and after the preservation was measured using a reflection densitometer (X-Rite 310TR) and evaluated as a retention rate of pigment. The retention rate of pigment was evaluated at three points of reflection density of 1, 1.5 and 2. The case where the retention rate of pigment was 90% or more at any of the densities was designated as A, the case where the retention rate of pigment was less than 90% at the two points was designated as B, and the case where the retention rate of pigment was less than 90% at all of the densities was designated as C, respectively.

<Resistance to Ozone Gas>

The photographic glossy paper having an image formed thereon was allowed to stand for 14 days in a box placed in a dark place at room temperature in an ozone gas concentration of 0.5±0.1 ppm while passing dry air through a double glass tube of a Siemens type ozonizer and applying an alternating current of 5 kV, and the image density before and after standing under the ozone gas stream was measured using a reflection densitometer (X-Rite 310TR) and evaluated as a retention rate of pigment. The retention rate of pigment was evaluated at three points of reflection density of 1, 1.5 and 2. The ozone gas concentration in the box was set up using an ozone gas monitor manufactured by APPLICS (Model: OZG-EM-01).

The retention rate of pigment was evaluated according to the following three grades. That is, the case where the retention rate of pigment was 70% or more at any of the densities was designated as A, the case where the retention rate of pigment was less than 70% at one or two points was designated as B, and the case where the retention rate of pigment was less than 70% at all of the densities was designated as C, respectively.

<Ink Storage Stability>

With respect to the ink, the tests of storage stability and recovery of clogging were carried out, thereby evaluating solubility of the dye. With respect to the ink storage stability, each of the Ink Solutions was charged in a polyethylene-made container, and a cycle of storing under conditions of −15° C. for 24 hours and subsequently storing under conditions of 60° C. for 24 hours {−15° C. (24 hr.)→60° C. (24 hr.)} was repeated 10 times. Thus, the presence or absence of deposition of insoluble matters before and after the storage was examined and evaluated according the following criteria.

[Evaluation Criteria]

The recording solution after elapsing was taken in a test tube and visually observed.

A: The state where insoluble matters are not found at all.
B: The state where a small amount of insoluble matters are found.
C: The state where insoluble matters are remarkably found, the level of which is not practically useful.

<Recovery of Clogging>

Each of the inks was filled in a printer and allowed to stand in the atmosphere at 40° C. for one month in the state where no cap was applied. After standing, the recovery of clogging was evaluated from the number of motions of cleaning required such that all nozzles normally ejected the ink according to the following criteria.

[Evaluation Criteria]

A: The nozzles are recovered by cleaning within two times.
B: The nozzles are recovered after recovering of three to five times.
C: The nozzles are recovered after cleaning of six or more times.
NG: The nozzles are not recovered.

<Solubility>

The dye was mixed with 5 mL of distilled water and stirred for 30 minutes using a magnetic stirrer. After stirring, whether or not the dye had been completely dissolved in the solvent was confirmed. The evaluation was made according to three grades as defined below.

A: The dye (0.5 g) is completely dissolved in 5 mL of the solvent.

B: The dye (0.5 g) is not completely dissolved in 5 mL of the solvent, but 0.1 g of the dye is completely dissolved therein.

C: The dye (0.1 g) is not completely dissolved in 5 mL of the solvent.

<Oxidation Potential: Eox>

The values of oxidation potential of the phthalocyanine dyes (or mixtures) used in the Examples and Comparative Examples were measured under the following conditions.

The phthalocyanine dye was weighed in the range of from 10.0 mg to 25.0 mg, and the oxidation potential was measured in from 5 mL to 15 mL of N,N-dimethylformamide containing 0.1 moles/dm$^3$ (concentration of the dye: about 0.001 moles/dm$^3$) of tetrapropylammonium perchlorate as a supporting electrode by means of direct current polarography. As a polarographic device, a carbon (GC) electrode was used as a working electrode, and a rotary platinum electrode was used as a counter electrode. An oxidation wave obtained by sweeping the oxidation side (noble side) was subjected to linear approximation, and a middle point between an intersection with its peak value and an intersection with its residual current value was made a value of oxidation potential (vs SCE).

The evaluation was made according to the following criteria. That is, the case where the oxidation potential was 1.0 or more was designated as "A", and the case where it was less than 1.0 was designated as "C", respectively.

As is clear from Table 6, the inkjet inks of the invention were excellent in color tone, small in paper dependency, and excellent in resistance to water, resistance to light and resistance to ozone. Especially, it is evident that the inkjet inks of the invention are excellent in image preservability such as resistance to light and resistance to ozone.

Also, it has been understood that the ink solutions according to the preparation method of the invention are free from deterioration of printings due to deposition of low dissolution components even when exposed under severe storage conditions and are excellent in ink storage stability and recovery of clogging.

Example 5

Using each of the inks prepared in Example 4, an image was printed on an inkjet paper photographic glossy paper EX manufactured by Fuji Photo Film Co., Ltd. by the same device as in Example 4 and evaluated in the same manners as in Example 4. As a result, the same results as in Example 4 were obtained.

Example 6

Each of the inks prepared in Example 4 was filled in a cartridge of an inkjet printer BJ-F850 (manufactured by CANON), printed on a photographic glossy paper GP-301 manufactured by CANON by the same printer, and then evaluated in the same manners as in Example 4. As a result, the same results as in Example 4 were obtained.

Example 7

The same test as in Example 4 was followed, except that the test method of Example was changed to the following environmental test method. That is, as a test method of resistance to an oxidizing gas of simulating oxidizing gases such as exhaust gases of automobile and outdoor environment where sunlight is irradiated, the test was carried out in an oxidation resistance test method using a fluorescent lamp irradiating chamber having a relative humidity of 80% and a hydrogen peroxide concentration of 120 rpm as described in H. Iwano, et al., *Journal of Imaging Science and Technology*, Vol. 38, pages 140 to 142 (1944). As a result of the test, the same results as in Example 4 were obtained.

The invention brings about the following advantages.

(1) By using a phthalocyanine compound that has a specific structure as a coloring agent, an ink that has an absorption characteristic excellent in color reproducibility, has sufficient fastness to light, heat, humidity and active gases in the environment, and is useful as a printing ink for inkjet recording, etc. is provided.

(2) The foregoing coloring composition is excellent in long-term storage stability of ink, has high dissolution stability of dissolution components, does not cause clogging of nozzles, and is excellent in quick drying of a material to be recorded.

(3) By the use of the foregoing coloring composition, an inkjet ink capable of forming an image having good hue and having high fastness to light and active gases in the environment, especially ozone gas and an inkjet recording method are provided.

(4) By utilizing the foregoing inkjet recording method, a method of improving resistance to color fading by ozone gas of an image-recorded matter is provided.

This application is based on Japanese Patent application JP 2003-421124, filed Dec. 18, 2003, the entire content of which is hereby incorporated by reference, the same as if set forth at length.

What is claimed is:

1. An ink containing a phthalocyanine compound represented by the formula (I):

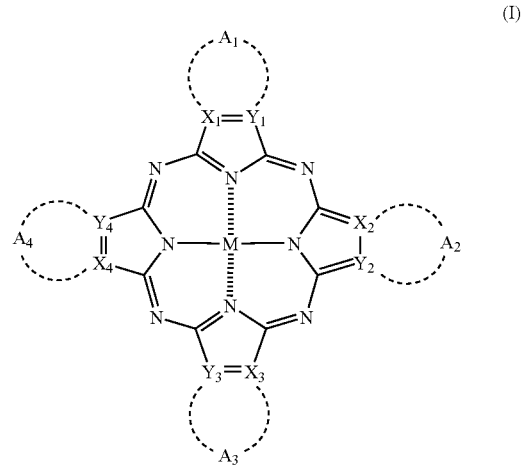

wherein $X_1$ to $X_4$ and $Y_1$ to $Y_4$ each independently represents a carbon atom or a nitrogen atom, $A_1$ to $A_4$ each independently represents an atomic group necessary for forming an aromatic ring or a heterocyclic ring together with $X_1$ to $X_4$ and $Y_1$ to $Y_4$, and at least one of the four rings containing $A_1$, $X_1$ and $Y_1$; $A_2$, $X_2$ and $Y_2$; $A_3$, $X_3$ and $Y_3$; and $A_4$, $X_4$ and $Y_4$ is an aromatic ring represented by the formula (V-1), provided that all of four rings containing $A_1$, $X_1$ and $Y_1$; $A_2$, $X_2$ and $Y_2$; $A_3$, $X_3$ and $Y_3$; and $A_4$, $X_4$ and $Y_4$ do not represent an aromatic ring at the same time:

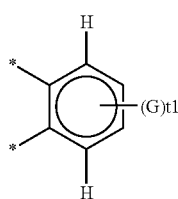
(V-1)

in which G represents —SO-$Z_1$, —SO$_2$-$Z_1$, —SO$_2$N$Z_1Z_2$, —CON$Z_1Z_2$, —CO$_2Z_1$ or —CO$Z_1$; t1 represents an integer of 1 or 2; $Z_1$'s may be the same or different and each represents a substituted or unsubstituted alkyl group having from 1 to 20 carbon atoms in total, a substituted or unsubstituted cycloalkyl group having from 3 to 20 carbon atoms in total, a substituted or unsubstituted alkenyl group having from 2 to 20 carbon atoms in total, a substituted or unsubstituted alkynyl group having from 2 to 12 carbon atoms in total, a substituted or unsubstituted aralkyl group having from 7 to 20 carbon atoms in total, a substituted or unsubstituted aryl group having from 6 to 20 carbon atoms in total, or a substituted or unsubstituted heterocyclic group having from 4 to 20 carbon atoms in total: $Z_2$'s may be the same or different and each represents a hydrogen atom, a substituted or unsubstituted alkyl group having from 1 to 20 carbon atoms in total, a substituted or unsubstituted cycloalkyl group having from 3 to 20 carbon atoms in total, a substituted or unsubstituted alkenyl group having from 2 to 20 carbon atoms in total, a substituted or unsubstituted alkynyl group having from 2 to 12 carbon atoms in total, a substituted or unsubstituted aralkyl group having from 7 to 20 carbon atoms in total, a substituted or unsubstituted aryl group having from 6 to 20 carbon atoms in total, or a substituted or unsubstituted heterocyclic group having from 4 to 20 carbon atoms in total: and * represents a binding site to a phthalocyanine skeleton, $A_1$ to $A_4$ may each have a substituent; and at least one of $A_1$ to $A_4$, or at least one of substituents of $A_1$ to $A_4$ has an ionically hydrophilic group as a substituent, and M represents a hydrogen atom, a metal element, a metal oxide, a metal hydroxide, or a metal halide.

2. The ink of claim 1, wherein the phthalocyanine compound of the formula (I) is a phthalocyanine compound represented by the formula (II):

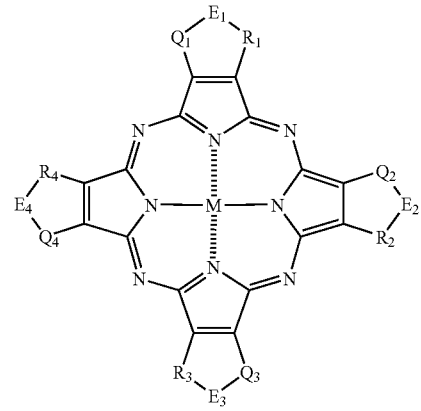
(II)

wherein $Q_1$ to $Q_4$ and $R_1$ to $R_4$ each independently represents a carbon atom, a nitrogen atom, a sulfur atom, an oxygen atom, or a phosphorus atom, $E_1$ to $E_4$ each independently represents an atomic group necessary for forming an aromatic ring or a heterocyclic ring together with $Q_1$ to $Q_4$ and $R_1$ to $R_4$, at least one of the four rings containing $E_1$, $Q_1$ and $R_1$; $E_2$, $Q_2$ and $R_2$; $E_3$, $Q_3$ and $R_3$; and $E_4$, $Q_4$ and $R_4$ is an aromatic ring represented by the formula (V-1), provided that all of four rings containing $E_1$, $Q_1$ and $R_1$; $E_2$, $Q_2$ and $R_2$; $E_3$, $Q_3$ and $R_3$; and $E_4$, $Q_4$ and $R_4$ do not represent an aromatic ring at a same time; $E_1$ to $E_4$ may each have a substituent; and at least one of $E_1$ to $E_4$, or at least one of substituents of $E_1$ to $E_4$ has an ionically hydrophilic group as a substituent.

3. The ink of claim 2, wherein the phthalocyanine compound of the formula (II) is a phthalocyanine compound represented by the formula (III):

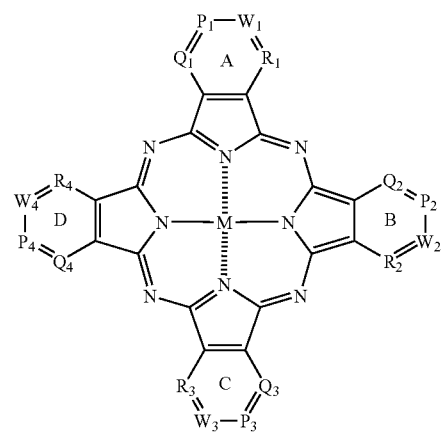
(III)

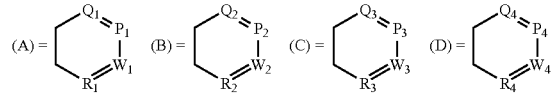

wherein $Q_1$, $P_1$, $W_1$ and $R_1$ each independently represents =C($J_1$)- or —N=, $Q_2$, $P_2$, $W_2$ and $R_2$ each independently represents =C($J_2$)- or —N=, $Q_3$, $P_3$, $W_3$ and $R_3$ each independently represents =C($J_3$)- or —N=, and $Q_4$, $P_4$, $W_4$ and $R_4$ each independently represents =C($J_4$)- or —N=, $J_1$ to $J_4$ each independently represents a hydrogen atom or a substituent, at least one of the four rings of: ring (A) containing $Q_1, P_1, W_1, R_1$; ring (B) containing $Q_2, P_2, W_2, R_2$; ring (C) containing $Q_3, P_3, W_3, R_3$; and ring (D) containing $Q_4, P_4, W_4, R_4$ is an aromatic ring represented by the formula (V-1), provided that a case where all four rings of: ring (A) containing $Q_1, P_1, W_1, R_1$; ring (B) containing $Q_2, P_2, W_2, R_2$; ring (C) containing $Q_3, P_3, W_3, R_3$; and ring (D) containing $Q_4, P_4, W_4, R_4$, respectively represent an aromatic ring at a same time is excluded; in a case where $J_1$ to $J_4$ each represents a substituent, the substituent may further have a substituent; and at least one of $J_1$ to $J_4$, has an ionically hydrophilic group as a substituent, and M represents a hydrogen atom, a metal element, a metal oxide, a metal hydroxide, or a metal halide.

4. The ink of claim 3, wherein a heterocyclic ring of at least one the four rings (A), (B), (C) and (D) is represented by the formula (IV):

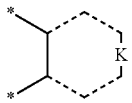

(IV)

wherein K represents an atomic group necessary for forming a 6-membered nitrogen-containing heterocyclic ring.

5. The ink of claim 3, wherein at least one of the four rings (A), (B), (C) and (D) represents a pyridine ring or a pyrazine ring.

6. The ink of claim 1, wherein the ink is an inkjet recording ink.

7. An inkjet recording method comprising forming an image on an image receiving material comprising a support and an ink receiving layer containing white inorganic pigment particles, with the inkjet recording ink of claim 6.

8. An image forming method comprising forming an image with the ink of claim 1.

9. A phthalocyanine compound represented by the formula (III):

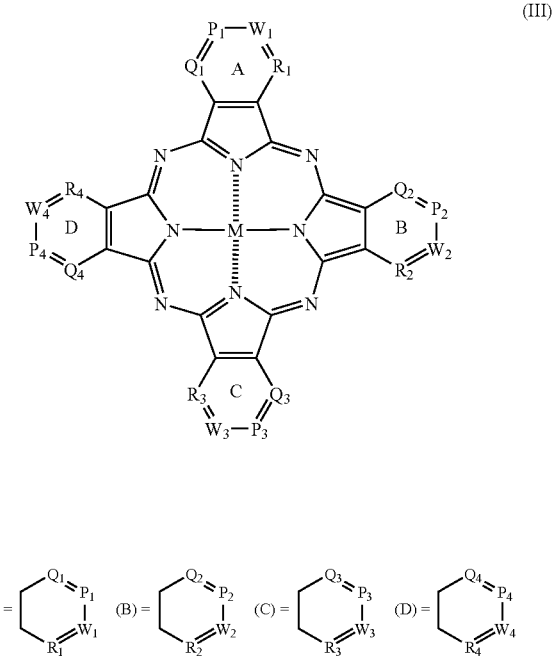

(III)

wherein $Q_1$, $P_1$, $W_1$ and $R_1$ each independently represents =C($J_1$)- or —N=, $Q_2$, $P_2$, $W_2$ and $R_2$ each independently represents =C($J_2$)- or —N=, $Q_3$, $P_3$, $W_3$ and $R_3$ each independently represents =C($J_3$)- or —N=, and $Q_4$, $P_4$, $W_4$ and $R_4$ each independently represents =C ($J_4$)- or —N=, $J_1$ to $J_4$ each independently represents a hydrogen atom or a substituent, at least one of the four rings of: ring (A) containing $Q_1, P_1, W_1 R_1$; ring (B) containing $Q_2, P_2, W_2 R_2$; ring (C) containing $Q_3, P_3, W_3 R_3$; and ring (D) containing $Q_4, P_4, W_4, R_4$ is an aromatic ring represented by the formula (V-1):

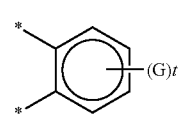

(V)

in which G represents —SO-$Z_1$, —$SO_2$-$Z_1$, —$SO_2NZ_1Z_2$, —$CONZ_1Z_2$, —$CO_2Z_1$ or —$COZ_1$; t1 represents an integer of 1 or 2; $Z_1$'s may be the same or different and each represents a substituted or unsubstituted alkyl group having from 1 to 20 carbon atoms in total, a substituted or unsubstituted cycloalkyl group having from 3 to 20 carbon atoms in total, a substituted or unsubstituted alkenyl group having from 2 to 20 carbon atoms in total, a substituted or unsubstituted alkynyl group having from 2 to 12 carbon atoms in total, a substituted or unsubstituted aralkyl group having from 7 to 20 carbon atoms in total, a substituted or unsubstituted aryl group having from 6 to 20 carbon atoms in total, or a substituted or unsubstituted heterocyclic group having from 4 to 20 carbon atoms in total: $Z_2$'s may be the same or different and each represents a hydrogen atom, a substituted or unsubstituted alkyl group having from 1 to 20 carbon atoms in total, a substituted or unsubstituted cycloalkyl group having from 3 to 20 carbon atoms in total, a substituted or unsubstituted alkenyl group having from 2 to 20 carbon atoms in total, a substituted or unsubstituted alkynyl group having from 2 to 12 carbon atoms in total, a substituted or unsubstituted aralkyl group having from 7 to 20 carbon atoms in total, a substituted or unsubstituted aryl group having from 6 to 20 carbon atoms in total, or a substituted or unsubstituted heterocyclic group having from 4 to 20 carbon atoms in total; and * represents a binding site to a phthalocyanine skeleton, provided that a case where all four rings of: ring (A) containing $Q_1$, $P_1$, $W_1$, $R_1$; ring (B) containing $Q_2$, $P_2$, $W_2$, $R_2$; ring (C) containing $Q_3$, $P_3$, $W_3$, $R_3$; and ring (D) containing $Q_4$, $P_4$, $W_4$, $R_4$, respectively represent an aromatic ring at a same time is excluded; in a case where $J_1$ to $J_4$ each represents a substituent, the substituent may further have a substituent; and at least one of $J_1$ to $J_4$, or at least one of substituents of $J_1$ to $J_4$ has an ionically hydrophilic group as a substituent, and M represents a hydrogen atom, a metal element, a metal oxide, a metal hydroxide, or a metal halide.

* * * * *